(12) United States Patent  
Billadeau et al.

(10) Patent No.: US 7,776,583 B2  
(45) Date of Patent: Aug. 17, 2010

(54) METHODS AND APPARATUSES FOR CONDUCTING ASSAYS

(75) Inventors: Mark A. Billadeau, Knoxville, MD (US); Jeff D. Debad, Gaithersburg, MD (US); Eli N. Glezer, Chevy Chase, MD (US); Jonathan K. Leland, Silver Spring, MD (US); Charles A. Wijayawardhana, Giessen (DE)

(73) Assignee: Meso Scale Technologies, LLC, Gaithersburg, MD (US)

( * ) Notice: Subject to any disclaimer, the term of this patent is extended or adjusted under 35 U.S.C. 154(b) by 1038 days.

(21) Appl. No.: 11/145,528

(22) Filed: Jun. 3, 2005

(65) Prior Publication Data

US 2006/0019319 A1    Jan. 26, 2006

Related U.S. Application Data

(60) Provisional application No. 60/576,710, filed on Jun. 3, 2004.

(51) Int. Cl.
*C12M 1/36* (2006.01)
*G01N 33/53* (2006.01)
*G01N 35/08* (2006.01)

(52) U.S. Cl. .......... 435/286.5; 435/3; 435/7.1; 435/286.1; 435/286.7; 435/287.2; 436/517; 436/52; 436/164; 436/165; 436/172; 436/175; 436/177; 422/68.1; 422/82.01; 422/82.05; 422/82.08

(58) Field of Classification Search .......... 435/5, 435/6, 7.1, 7.25, 7.5, 7.92–7.94, 173.9, 287.2, 435/287.3, 288.5, 968; 436/517, 524, 528, 436/532, 537, 538, 540, 164, 165, 172, 175, 436/177; 422/52, 63, 68.1, 82.01, 82.05, 422/82.08, 93
See application file for complete search history.

(56) References Cited

U.S. PATENT DOCUMENTS

| 4,168,146 | A | 9/1979 | Grubb et al. |
| 4,235,601 | A | 11/1980 | Deutsch et al. |

(Continued)

FOREIGN PATENT DOCUMENTS

WO     WO 95/27208    * 10/1995

(Continued)

OTHER PUBLICATIONS

Piironen et al., Measurement of Circulating Forms of Prostate-specific Antigen in Whole Blood Immediately after Venipuncture: Implications for Point-of-Care Testing, Clinical Chemistry 47 (4): 703-711 (2001).*

(Continued)

*Primary Examiner*—Gailene R Gabel
(74) *Attorney, Agent, or Firm*—Wolf, Greenfield & Sacks, P.C.

(57) ABSTRACT

Disclosed are methods for conducting assays of samples, such as whole blood, that may contain cells or other particulate matter. Also disclosed are systems, devices, equipment, kits and reagents for use in such methods. One advantage of certain disclosed methods and systems is the ability to rapidly measure the concentration of an analyte of interest in blood plasma from a whole blood sample without blood separation and hematocrit correction.

54 Claims, 10 Drawing Sheets

U.S. PATENT DOCUMENTS

| | | | |
|---|---|---|---|
| 4,366,241 | A | 12/1982 | Tom et al. |
| 4,442,204 | A | 4/1984 | Greenquist et al. |
| 5,208,535 | A | 5/1993 | Nakayama et al. |
| 5,460,945 | A * | 10/1995 | Springer et al. ............ 435/7.24 |
| 6,106,778 | A | 8/2000 | Oku et al. |
| 6,475,372 | B1 | 11/2002 | Ohara et al. |
| 7,497,997 | B2 | 3/2009 | Glezer et al. |

FOREIGN PATENT DOCUMENTS

| | | |
|---|---|---|
| WO | WO 95/27208 A1 | 10/1995 |

OTHER PUBLICATIONS

Bitsch, L., "Blood Flow in Microchannels," Master Thesis, Technical University of Denmark, pp. 1-93 (Sep. 3, 2002).

Boryczko, K., et al., "Dynamical clustering of red blood cells in capillary vessels," *J Mol Model*, vol. 9, pp. 16-33 (2003).

Piironen, T., et al., "Measurement of Circulating Forms of Prostate-specific Antigen in Whole Blood Immediately after Venipuncture: Implications for Point-of-Care Testing," *Clinical Chemistry*, vol. 47, No. 4, pp. 703-711 (2001).

Tarkkinen, P., et al., "Ultrarapid, Ultrasensitive One-Step Kinetic Immunoassay for C-Reactive Protein (CRP) in Whole Blood Samples: Measurement of the Entire CRP Concentration Range with a Single Sample Dilution," *Clinical Chemistry*, vol. 48, No. 2, pp. 269-277 (2002).

International Search Report and Written Opinion of the International Searching Authority, dated Oct. 24, 2005 for corresponding International Application No. PCT/US2005/019498.

Official Communication dated Oct. 16, 2007 and Claims as Pending for corresponding European Patent Application No. 05759189.3.

Hochman, J. et al., "An Active Antibody Fragment (Fv) Composed of the Variable Portions of Heavy and Light Chains," *Biochemistry* 1973, vol. 12, No. 6, 1130-1135.

Porter, R. et al., "Subunits of Immunoglobulins and their Relationship to Antibody Specificity," *J. Cell. Physiol.* 67 (Sup. 1), 51-64, (Feb. 4, 2005).

Pries, A. et al., "Blood viscosity in tube flow: dependence on diameter and hematocrit," *The American Physiological Society* 1992, 0363-6135/92, H1770-H1778.

* cited by examiner

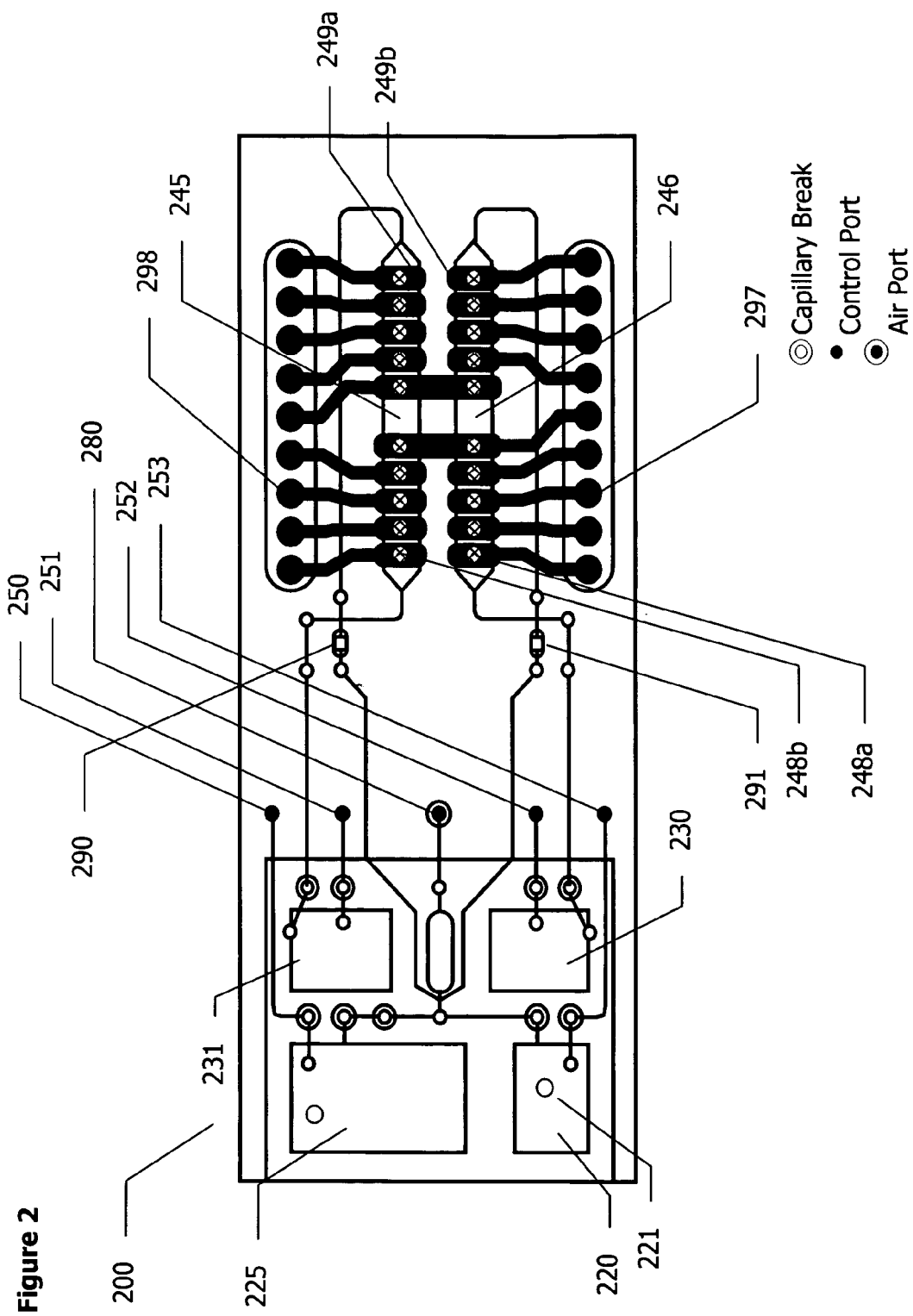

METHODS AND APPARATUSES FOR CONDUCTING ASSAYS

RELATED APPLICATIONS

This application claims the benefit of priority to: U.S. Provisional Patent Application Ser. No. 60/576,710, filed Jun. 3, 2004, titled METHODS AND APPARATUSES FOR CONDUCTING ASSAYS, by M. Billadeau, et al., which is incorporated herein by reference.

FIELD OF THE INVENTION

The present invention is directed to methods for conducting assays of samples, such as whole blood, that may contain cells or other particulate matter. The invention also relates to systems, devices, equipment, kits and reagents for use in such methods.

BACKGROUND OF THE INVENTION

Traditionally, clinical measurements (especially, solid phase binding assays) for analytes in blood have been carried out in serum or plasma samples derived from the blood. Partly for this reason, clinicians present the levels of most blood markers in terms of the concentration of the marker in the liquid fraction of the blood sample (e.g., the concentration in plasma or serum fractions derived from the blood sample). Assays carried out in whole blood have had limited acceptance, in part because conventional assays give different signals for a whole blood sample relative to a plasma or serum fraction derived from the same sample. This difference is primarily due to the difference in concentration of the analyte in the different sample types: the concentration of an analyte in a whole blood sample being effectively diluted relative to the concentration of the analyte in the liquid fraction because of the volume occupied by the red blood cells. The difference in signals makes it difficult to compare results to well established reference ranges that have been expressed in terms of the concentration of the analyte in serum or plasma. In addition, the presence of a large volume fraction of cells in a whole blood sample may also interfere with many assay technologies and make it difficult to carry out precise and accurate measurements.

Piironen T, et. al., (2001) *Clinical Chem.*, 74 (4): 703-711 and Tarkkinen, P., et al., (2002) *Clinical Chem.*, 48 (2) 269-277) disclosed, respectively, immunoassays of whole blood samples for prostate specific antigen and C-reactive protein (CRP). Both references report correlation curves comparing the measured levels of the analytes in whole blood relative to the measured levels in the corresponding plasma or serum fractions. In both cases, the authors reported that the graphs could be fit by lines with slopes of roughly 0.56-0.57, the difference from unity being attributed to the average hematocrit (the relative volume of blood occupied by erythrocytes) of the whole blood samples. The authors propose correcting measurements in whole blood samples using the assumption that the samples have a hematocrit value equal to the average hematocrit for the patient population. Because of the wide range for hematocrit values that may be observed in patient samples (the normal range is from 41-50% for adult males and 35-46% for adult females, but hematocrit levels of less than 20% can be observed in severe cases of anemia), this approach could lead to large errors in the reported values.

U.S. Pat. No. 6,475,372 to Ohara T J et al.; U.S. Pat. No. 6,106,778 to Oku N. et al. disclose apparatuses for measuring both the concentration of an analyte in a whole blood sample and the hematocrit of the sample. The measured concentration value is converted to the concentration of analyte in the liquid fraction by using the measured hematocrit value to apply a hematocrit correction. This approach adds complexity to the assay apparatus and may be subject to increased imprecision because the error is a function of the variability in both the assay signal and hematocrit determination.

Other approaches developed for conducting assays on whole blood samples have used instrumentation that employ integrated filters (including lateral flow membranes) or centrifuges to provide for separation of the red blood cells from plasma or serum fractions prior to the measurement of the analyte. While these approaches avoid the need for a hematocrit correction, they add significant cost and complexity to the instrumentation. In addition, filtration has the disadvantages of possible loss of analyte to the filter material and limitations in the sample volume that can be easily processed.

SUMMARY OF THE INVENTION

The invention relates to methods for conducting assays for measuring analytes in samples, which samples may contain particulate matter, and related apparatus. The invention includes methods that permit the measurement of the concentration of an analyte in the liquid fraction of the sample. This measurement may be carried out without removing the particulate matter from the sample and/or without correcting the results to account for the volume of the sample occupied by the particulate matter. In many cases, the measurement of the concentration of an analyte in the liquid fraction of the sample performed according to certain inventive methods, e.g. without prior removal of the particulate matter from the sample and/or without correcting the results to account for the volume of the sample occupied by the particulate matter, closely approximates, nearly equals, or equals the actual concentration of the analyte in the liquid fraction of the contiguous sample (i.e. as would be measured for a sample consisting of the pure liquid fraction from which essentially all particulate matter was removed prior to the measurement). In certain embodiments, the concentration of the analyte in the sample as measured using the inventive methods will differ from the actual concentration of the analyte in the liquid fraction of the sample by no more than 20%, 10%, 5%, 2%, 1%, 0.5%, or even less. According to one embodiment, samples differing greatly in the volume fraction occupied by particulate matter may be analyzed without measuring or requiring knowledge of the value of the volume fraction. The invention also relates to systems, devices, equipment, kits and reagents for use in such methods.

One embodiment of the invention relates to a method for measuring one or more analytes of interest comprising exposing a sample containing particulate matter to a surface, such as a binding surface, so that at least a portion of the sample, contacts the surface, optionally immobilizing an amount of an analyte on the surface, and measuring the amount of analyte on the surface. For example, a portion consisting of or consisting essentially of the liquid fraction of the contiguous volume of a sample may contact the surface. The measured amount is dependent on the concentration of the analytes in the liquid fraction of the sample and is substantially independent of the volume occupied by particulate matter in the sample.

Another embodiment of the invention relates to a method for measuring one or more analytes of interest comprising exposing a sample containing particulate matter to a surface, such as a binding surface, so that at least a portion of the sample contacts the surface, optionally immobilizing an amount of an analyte on said surface and measuring the amount of the analyte immobilized on the surface, and determining a concentration of the analyte in the sample that differs from the actual concentration of the analyte the liquid fraction of the sample by no more than 20%, 10%, 5%, 2%, 1%, or 0.5%. For example, a portion consisting of or consisting essentially of the liquid fraction of the contiguous volume of a sample may contact the surface. The determination is achieved without correcting for the volume of the sample occupied by particulate matter.

Yet another embodiment of the invention relates to a method for measuring one or more analytes of interest comprising exposing a sample containing particulate matter to a surface, such as a binding surface, so that at least a portion of the sample contacts the surface, immobilizing an amount of an analyte on the surface and generating an assay signal that is indicative of the amount of the analyte immobilized on the surface. For example, a portion consisting of or consisting essentially of the liquid fraction of the contiguous volume of a sample may contact the surface. The assay signal is dependent on the concentration of the analyte in the liquid fraction of the sample and is substantially independent of the volume occupied by particulate matter in the sample.

Yet another embodiment of the invention relates to a method for measuring one or more analytes of interest comprising exposing a sample containing particulate matter to a surface, such as a binding surface, so that at least a portion of the sample contacts the surface, immobilizing an amount of an analyte on the surface, generating an assay signal that is indicative of the amount of the analyte immobilized on the surface and determining, from the measured amount, a concentration of the analyte in the sample that differs from the actual concentration of the analyte the liquid fraction of the sample by no more than 20%, 10%, 5%, 2%, 1%, or 0.5%. For example, a portion consisting of or consisting essentially of the liquid fraction of the contiguous volume of a sample may contact the surface. The determination is achieved without correcting for the volume occupied by particulate matter.

Yet another embodiment of the invention relates to a method for measuring one or more analytes of interest comprising determining, in a particle-containing fluid sample comprising a fluid fraction and a plurality of particles suspended therein and containing the analyte, a measurement of the concentration of the analyte present in the fluid fraction that is substantially independent of the volume of the particles suspended in the fluid sample.

The assay methods of the invention are suitable for measuring the plasma concentration of analytes in whole blood samples without a separate step of separating the red blood cells and/or without correcting for hematocrit. In certain embodiments, a solid phase binding assay for determining the plasma concentration is used. In certain such embodiments of solid phase binding assays of the invention, the amount of an analyte immobilized on a binding surface and any corresponding assay signal indicative of this amount, is dependent on the plasma concentration of analyte in a whole blood sample and is independent of the hematocrit of the sample. In many cases, the measurement of the plasma concentration of the whole blood sample performed according to certain inventive methods, e.g. without prior removal of the blood cells from the sample and/or without correcting the results to account for hematocrit, closely approximates, nearly equals, or equals the actual plasma concentration of the analyte (i.e. as would be measured for a sample consisting of the pure plasma fraction from which essentially all blood cells were removed prior to the measurement). In certain embodiments, the concentration of the analyte in the sample measured using the inventive methods will differ from the actual plasma concentration of the analyte by no more than 20%, 10%, 5%, 2%, 1%, 0.5%, or even less.

In certain assay methods of the invention, the act of contacting at least a portion of a sample with a binding surface may comprise contacting the sample with a plurality of binding domains on one or more binding surfaces, where the binding domains have different specificity for analytes of interest. Accordingly, the assay methods may further comprise measuring one or more additional analytes in the sample. In one embodiment, each analyte of interest is immobilized in a different binding domain and the amount of each analyte in the corresponding binding domain is measured, e.g., by measuring an assay signal indicative of the amount of immobilized analyte.

In certain embodiments, the immobilization is performed over an interval of time, for example an interval of time less than 10 minutes, or less than 5 minutes. During this interval of time, only a fraction of the analyte present in the sample may be, immobilized. In certain embodiments, less than 30% of an analyte, less than 20% of an analyte and less than 10% of an analyte in a sample is immobilized on the binding surface.

The assay methods of the invention may include calibrating the assay using calibrator samples with known concentrations of said analyte. These calibrator samples may be free of particulate matter. For example, in the case of assays suitable for use with whole blood samples, the calibrator samples may be substantially free of red blood cells.

The assay methods may employ a variety of assay formats including sandwich assay and/or competitive assay formats.

The binding surfaces (or binding domains within a binding surface) may comprise a binding reagent immobilized thereon. This binding reagent may bind to an analyte of interest. The binding of the analyte of interest to the binding reagent on the surface may be direct or may occur via one or more bridging reagents. Accordingly, the assay methods of the invention may include contacting the sample with a bridging reagent that binds both the binding reagent immobilized on the binding surface and an analyte.

The assay methods of the invention may further comprise contacting an analyte of interest with i) a labeled binding reagent that binds the analyte and/or ii) a labeled competitor of the analyte. The binding reagent or competitor, may be labeled with a label such as, without limitation, ECL labels, luminescent labels, fluorescent labels, phosphorescent labels, radioactive labels, enzyme labels, electroactive labels, magnetic labels and light scattering labels.

The binding surfaces used in the solid phase binding assay methods of certain embodiments of the invention may be surfaces within a flow cell. The binding surfaces may include one or more electrode surfaces, which may be located within a flow cell. The binding surfaces used in the methods of the invention may be rough. In certain embodiments, the surfaces are sufficiently rough so that the surface area accessible to an analyte is at least two-fold larger than the surface area accessible to red blood cells.

The solid phase binding assay methods of certain embodiments of the invention may include flowing the sample over the binding surface. The flowing act may include flowing the sample over the binding surface in a back and forth motion. In certain embodiments, the flow is laminar and/or is characterized by Reynold's numbers of less than 100, or, in certain embodiments, of less than 10. In certain embodiments of the invention, the flow of whole blood samples over a binding surface is carried out under conditions that provide a plasma-rich layer adjacent to the binding surface. In certain embodiments, the binding is carried out under conditions that do not deplete analyte from the sample.

In one particular embodiment such a method comprises creating a flow of a contiguous volume of a whole blood sample over a surface; thereby segregating blood cells contained in the sample away from the surface to create a first, plasma rich, region of the sample in contact with the surface and a second, cell rich, region of the sample separated from the surface by the first region, wherein the concentration of blood cells in the second region substantially exceeds the concentration of blood cells in the first region; and determining a concentration of an analyte of interest in fluid present in the first, plasma enriched, region. In another particular embodiment a method comprises acts of: (1) creating a flow of a whole blood sample, for example a contiguous volume of a whole blood sample, over a surface, wherein the blood flow segregates blood cells contained in the sample away from the surface to create a plasma enriched first region of the sample; and (2) determining a concentration of an analyte of interest in first region. A skilled artisan may readily recognize that the invention encompasses embodiments where the particulate (e.g. blood cell) concentration in the contiguous volume of a sample exists as a gradient, which may be a continuous gradient, over the cross-section of the flow channel; in such cases, the first and the second regions may comprise spatial designations representative of first and second fractions of the contiguous volume of the sample that have different volume-averaged particulate (e.g. blood cell) concentrations. For example, in one embodiment, a contiguous volume of a whole blood sample flowing in a flow cell of one embodiment of the invention has a gradient of blood cell concentration across the entirety of the contiguous volume of the sample, which gradient is characterized by the presence of a relatively plasma enriched fraction comprising a first region in contact and close proximity with an inner surface of the flow channel, and relatively cell enriched fraction comprising a second region separated from the inner surface by the first region.

In another embodiment, the binding surface is positioned in an assay cell (such as a flow cell) such that, during operation, the surface faces sidewise or, downward. Blood cells in a whole blood sample held in the assay cell can settle to the bottom of the cell and away from the binding surface so as to provide a plasma-rich layer adjacent the binding surface. In such an embodiment, the assay methods may include introducing a whole blood sample into the cell and allowing the red blood cells to settle. In certain embodiments, the binding is carried out under conditions that do not substantially deplete analyte from the sample.

In one particular embodiment, a method comprises exposing a whole blood sample to a surface, for example exposing a contiguous volume of a whole blood sample to a surface; maintaining blood cells contained in the sample away from at least a portion of the surface to create a first, plasma enriched, region of the sample in contact with the at least a portion of the surface and a second, cell enriched, region of the sample separated from the at least a portion of the surface by the first region, wherein the concentration of blood cells in the second region substantially exceeds the concentration of blood cells in the first region, and determining a concentration of an analyte of interest in fluid present in the first, plasma rich, region.

The assay methods of the present invention may further comprise displacing a sample from a binding surface prior to measuring the amount of one or more analytes immobilized on the surface or prior to generating an assay signal. Displacement of the sample may be carried out by introducing a wash solution. The assay methods may even further comprise contacting the binding surface with a solution containing a labeled binding reagent or labeled analog of an analyte after displacing the sample from the binding surface.

The assay methods of the invention may be carried out on undiluted samples, e.g., undiluted whole blood. In the case of whole blood samples, the blood sample may advantageously contain anticoagulants.

One specific embodiment of the present invention relates to a method for performing a rapid blood test, for example, a clinical diagnostic test, comprising i) drawing blood from a patient to provide a whole blood sample, ii) applying the whole blood sample to a cartridge having one or more binding surfaces having one or more binding domains, iii) flowing the sample over the binding surface(s) for a defined interval of time to immobilize amounts of one or more analytes, iv) measuring the amounts of the one or more analytes immobilized on the binding surface(s), which may be immobilized on one or more distinct binding assay domains and v) determining, from the measured amounts, the plasma concentrations of the one or more analytes in the sample. The method may be carried out without removing the red blood cells from the sample or correcting for sample hematocrit.

Also discussed are apparatuses that measure the concentration of an analyte in the liquid fraction of a sample e.g., the plasma concentration of an analyte in a whole blood sample). The apparatus may be configured to carry out the assay methods of the invention. The apparatus may comprise one or more binding surfaces having one or more binding domains and, optionally, one or more of the following additional components: a flow cell comprising the one or more binding surfaces, a pump for flowing sample past the binding surface(s), and a detector for detecting an assay signal.

Also discussed is a kit for measuring the concentration of an analyte in the liquid fraction of a sample (e.g., the plasma concentration of an analyte in a whole blood sample). The kit may be, configured to be suitable for use with the assay methods of the invention. The kit may comprise one or more binding surfaces having one or more binding domains and, optionally, one or more reagents such as labeled binding reagents that bind the analyte, labeled analogs of the analyte, anticoagulants, blocking agents, and pH buffers, etc. These components may be provided in dry form. The kit may also contain liquid components including wash buffers. The kit may further comprise an assay cartridge, which may be a disposable, containing the binding surface(s). The disposable cartridge may further comprise a flow cell comprising the binding surface(s). The cartridge may comprise a pump for moving sample over the binding surface(s) and/or a detector for detecting an assay signal. Alternatively, one or both of these components may be provided by a separate cartridge reader apparatus.

BRIEF DESCRIPTION OF DRAWINGS

The accompanying drawings are schematic are not intended to be drawn to scale. In the figures, each identical, or substantially similar component that is illustrated in various figures is typically represented by a single numeral or notation. For purposes of clarity, not every component is labeled in every figure, nor is every component of each embodiment of the invention shown where illustration is not necessary to allow those of ordinary skill in the art to understand the invention. In the drawings:

FIG. 2 shows a schematic representation of an assay cartridge according to one embodiment;

DETAILED DESCRIPTION OF THE INVENTION

Figure 1:
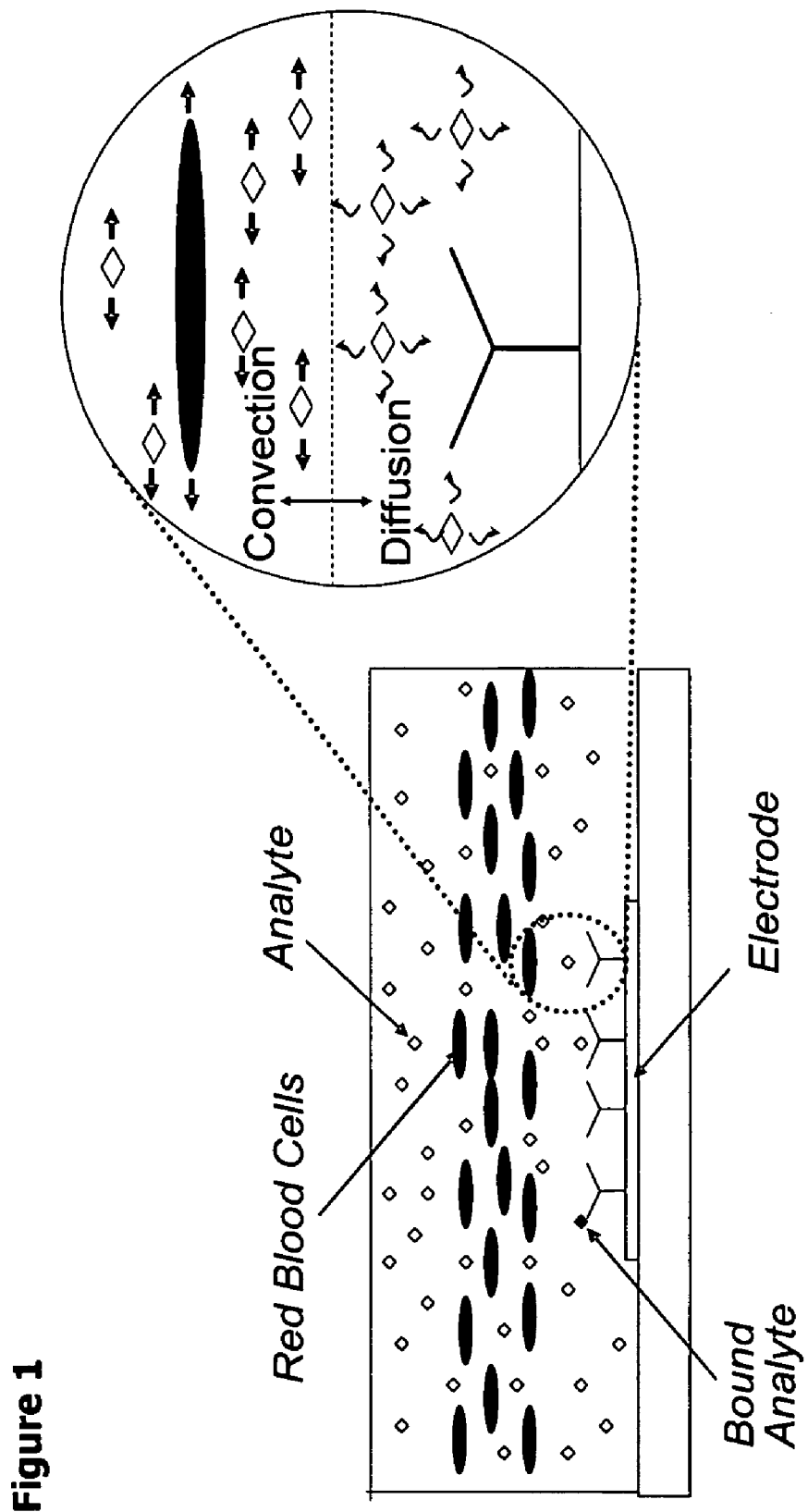
FIG. 1 shows a schematic representation of the flow of whole blood under conditions that result in the generation of a plasma-rich boundary region.

Disclosed are methods for conducting assays for measuring analytes in samples that may contain particulate matter. Certain embodiments of invention involve methods that permit the measurement of the concentration of an analyte in the liquid fraction of such samples. This measurement may be carried out without the need for prior removal of the particulate matter from the sample (e.g., without using centrifugation, settling, filtration (e.g., filtration through filters, porous membranes or lateral flow membranes), affinity binding, coagulation, etc. to remove the particulate matter) and/or without correcting the results to account for the volume of the sample occupied by the particulate matter. According to one embodiment, samples differing greatly in the volume fraction occupied by particulate matter may be analyzed to achieve a measure of the concentration of an analyte in the liquid fraction of the sample that can be equal to or closely approximating the actual concentration in the liquid fraction (i.e. as would be measured for a sample consisting of the pure liquid fraction from which essentially all particulate matter was removed prior to the measurement) without measuring or requiring knowledge of the value of the volume fraction occupied by the particles. In certain embodiments, the concentration of the analyte in the sample measure using the inventive methods will differ from the actual concentration of the analyte in the liquid fraction of the sample by no more 20%, 10%, 5%, 2%, 1%, 0.5%, or even less.

The methods of certain embodiments of the invention may be used to obtain a measurement of the plasma concentration of an analyte in a whole blood sample. According to one embodiment of the invention, the assay signal for a given plasma concentration of analyte in a whole blood sample is substantially independent of the hematocrit of the sample and substantially equivalent to the signal obtained for plasma or serum derived from the whole blood sample. Measurement of the concentration of one or more analytes in the plasma fraction of a whole blood sample can, therefore, be carried out without requiring the measurement of the hematocrit or the separation of plasma or serum fractions (e.g., without using centrifugation, settling, filtration, affinity binding, coagulation, etc. to remove the cellular fraction) prior to measurement.

"Measured," as used herein, may encompass quantitative and qualitative measurement, and may encompass measurements carried out for a variety of purposes including, but not limited to, detecting the presence of an analyte, quantitating the amount of an analyte, identifying a known analyte, and/or determining the identity of an unknown analyte in a sample.

The amount of an analyte in a sample may be presented as a concentration value, i.e., the amount per volume of sample. For samples containing particulate matter this concentration may be presented as amount per volume of whole sample, where the volume of whole sample includes the combined volumes of the liquid and particulate components of the sample. Alternatively, the concentration may be reported in terms of amount per volume of the liquid fraction or component of the sample.

Whole blood samples contain a liquid fraction (the plasma fraction) and a particulate fraction (a blood cell fraction comprised primarily of red blood cells or RBCs). The relative volumes of these two fractions have traditionally been measured by centrifuging whole blood and measuring the hematocrit, the ratio of the volume of the pellet (which approximates the volume of the blood cell fraction) to the total volume of the sample. The concentration of an analyte found in the plasma fraction can be expressed in terms of the whole blood concentration (a term that refers herein to the amount of analyte per volume of whole blood in a sample) or the plasma concentration (a term that refers herein to the amount of analyte per volume of plasma in a sample). The two concentrations are related by the following function: $C_{WB}=C_P(1-H)$, where $C_{WB}$ is the whole blood concentration, $C_P$ is the plasma concentration and H is the hematocrit for the sample. Traditionally, the plasma concentration of an analyte has been measured by first separating an aliquot of the plasma fraction from the blood cell fraction by filtration or centrifugation and then measuring the concentration of analyte in the plasma aliquot. In many clinical applications, the concentration of an analyte is presented as a serum concentration, i.e., the concentration of the analyte in serum derived from a whole blood sample. Serum is prepared by clotting whole blood and removing the remaining liquid fraction from the clot and cellular components. For analytes present in plasma that are not generated, consumed or bound during the clotting process, the plasma and serum concentrations are usually roughly equal.

Samples that may be analyzed by the methods of the invention include samples that contain or may potentially contain a large volume fraction of particulate matter (e.g., a high hematocrit in the case of whole blood samples). In one embodiment, a sample is analyzed that has, or may potentially have, a volume fraction of particulate matter (e.g., a hematocrit) between 10 and 80% or between 20 and 80% or between 20% and 60%. Examples of samples that may be analyzed include, but are not limited to, food samples, beverages, samples that comprise suspensions of dirt, environmental sludges or other environmental samples (such as suspensions of particles filtered, or otherwise concentrated, out of air samples, water samples, environmental swipes, etc.), and biological samples. Biological samples that may be analyzed include, but are not limited to, feces, mucosal swabs, physiological fluids and/or samples containing suspensions of cells. Specific examples of biological samples include tissue aspirates, tissue homogenates, cell cultures (including cultures of eukaryotic and prokaryotic cells), urine, cerebrospinal fluid, synovial fluid, amniotic fluid, pleural fluid, pericardial fluid, ascetic fluid and whole blood.

According to one embodiment, the sample is a whole blood sample. In certain embodiments, the whole blood sample is not diluted prior to analysis or the dilution kept to a minimum. In certain embodiments, the volume of a diluted whole blood sample relative to the volume of the whole blood sample prior to dilution is greater than 50%, or greater than 80%, or greater than 90%, or greater than 95%, or greater than 99% or 100% (i.e., the sample is undiluted). Reagents may be added to the whole blood sample prior to analysis, e.g., binding reagents (such as antibodies), agents that compete with an analyte for binding to a binding reagent, anticoagulants (e.g., heparin, citrate, oxalate, EDTA, etc.), pH buffering components, salts, blocking agents (e.g., proteins that block non-specific binding and/or block the binding of heterophile antibodies) and preservatives (e.g., fluoride, iodoacetate, etc.). The dilution of the whole blood sample may be minimized by adding these reagents in dry form or in liquid form in a small volume.

Advantageously, the methods of the invention allow the same methodology and apparatus to be used to measure samples with particulate matter (e.g., whole blood) and samples without particulate matter (e.g., plasma or serum) without requiring any corrections to be applied to account for the presence or absence of particles (e.g., a hematocrit correction). The assay methods of the invention may include an act of calibrating an assay by running calibration samples having known concentrations of analyte so as to determine the relationship between analyte concentration and assay signal. This calibration may be carried out by the end user or by the manufacturer of the assay reagents/kits/consumables/etc. The insensitivity of the assays of the invention to hematocrit can allow assays for whole blood samples to be calibrated with liquid, cell-free calibration samples, thus eliminating the need for storing calibration standards containing red blood cells and/or applying hematocrit corrections to the calibration parameters. Similarly, the assay methods of the invention may include the act of running one or more control samples to ensure the assay method is performing within specifications (proper performance being indicated by control signals that fall within pre-determined ranges). The insensitivity of the assays of the invention to hematocrit can allow for the use of cell-free controls for whole blood assays. By analogy, controls and/or calibrators for assays for other particulate containing samples can be run using particulate-free controls or calibrators.

In certain embodiments, of the invention, the methods include the act of exposing a sample, for example a contiguous volume of a sample, to a surface comprising an assay reagent and contacting at least a portion of the sample, e.g. a liquid fraction rich, particulate poor portion. Optionally, this surface may define, in part, the boundary of a container (e.g., a flow cell, well, cuvette, etc.) which holds the sample and/or through which the sample is passed. In one embodiment, the assay reagent comprises a reactant that reacts with an analyte in a sample. Suitable reactants include materials that covalently or non-covalently bind to an analyte or catalysts (e.g., enzymes) that catalyze a chemical reaction of an analyte. The method may also comprise measuring a signal that results from the chemical reaction, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc.

According to another embodiment of the invention, the methods comprise the acts of contacting at least a portion of a sample with a binding surface, immobilizing an analyte on the surface and measuring the analyte immobilized on the surface. In one example of such an embodiment, the binding surface is prepared by immobilizing, on a surface, binding reagents that bind the analyte. Optionally, the surface comprises an array of binding reagents. Optionally, the surface may define, at least in part, the boundary of a container (e.g., a flow cell, well, cuvette, etc.) which holds the sample or through which the sample is passed. The method may also comprise generating an assay signal that is indicative of the amount of the analyte on the surface, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc.

In certain embodiments the extent of a reaction with a reactant on a surface or the amount of an analyte of interest immobilized on a binding surface correlates with the concentration of analyte in the liquid fraction of the sample (e.g., the plasma concentration in a whole blood sample) but is substantially independent of the volume fraction of the sample occupied by particulate material (e.g., the hematocrit of a whole blood sample). Accordingly, the methods may further comprise the act of determining a measurement of the concentration of the analyte in the liquid fraction of the sample that equals or closely approximates the actual concentration of the analyte in the liquid fraction of the sample (i.e. as would be measured for a sample consisting of the pure liquid fraction from which essentially all particulate matter was removed prior to the measurement). This act may be performed without applying a hematocrit correction. According to one embodiment of the invention, i) the extent of the reaction of an analyte in a whole blood sample with a reactant on a surface and/or ii) the amount of an analyte immobilized on a binding surface from a whole blood sample is hematocrit independent and the measurement of this reaction or binding (or assay signal resulting from this reaction or binding) is indicative of the analyte concentration in the plasma fraction.

Certain embodiments include multiplexed measurements of multiple analytes in a sample. In one embodiment, the signal generated in response to the presence of different analytes has a distinguishable characteristic, e.g., wavelength of absorbance, energy of emission, current-voltage relationship, etc. that allows the signals to be deconvoluted or independently measured. In another embodiment, the analytes are measured by contacting a sample with assay reagents (e.g., binding reagents) that are present in spatially segregated assay domains (e.g., binding domains) on one or more surfaces, wherein at least two domains contain assay reagents that differ in their specificity for the analytes being measured. The spatial separation of the assay domains allows for independent measurement of assay signals generated at the different assay domains, e.g., through the wide variety of established optical, magnetic, radioactive and electrochemical techniques that have been established for conducting measurements using nucleic acid and protein arrays. In one specific embodiment, a sample is contacted with a surface comprising an array of assay domains, for example, an array of binding domains.

Also provided is a method comprising the act of contacting at least a portion of a sample with one or more surfaces comprising a plurality of assay domains. Optionally, these surfaces may define, at least in part, one or more boundaries of a container (e.g., a flow cell, well, cuvette, etc.) which holds the sample and/or through which the sample is passed. In one embodiment, the assay domains comprise reactants that react with analytes in a sample and at least two domains differ in their specificity for analytes of interest. Suitable reactants include materials that covalently or non-covalently bind to an analyte or catalysts (e.g., enzymes) that catalyzes a chemical reaction of an analyte. The method may also comprise measuring signals that result from the chemical reactions at the different domains, e.g., changes in optical absorbance, a change in fluorescence, the generation of chemiluminescence or electrochemiluminescence, a change in reflectivity, refractive index or light scattering, the accumulation or release of detectable labels from the domains, the oxidation or reduction or redox species, electrical currents or potentials, changes in magnetic fields, etc.

According to another embodiment of the invention, the methods comprise the acts of contacting at least a portion of a sample with one or more binding surfaces comprising a plurality of binding domains, immobilizing one or more analytes on the domains and measuring the analytes immobilized on the domains. In certain embodiments, at least two of the binding domains differ in their specificity for analytes of interest. In one example of such an embodiment, the binding domains are prepared by immobilizing, on one or more surfaces, discrete domains of binding reagents that bind analytes of interest. Optionally, the sample is exposed to a binding surface that comprises an array of binding reagents. Optionally, the surface(s) may define, in part, one or more boundaries of a container (e.g., a flow cell, well, cuvette, etc.) which holds the sample or through which the sample is passed. The method may also comprise generating assay signals that are indicative of the amount of the analytes in the different binding domains, e.g., changes in optical absorbance, changes in fluorescence, the generation of chemiluminescence or electrochemiluminescence, changes in reflectivity, refractive index or light scattering, the accumulation or release of detectable labels from the domains, oxidation or reduction or redox species, electrical currents or potentials, changes in magnetic fields, etc.

In certain embodiments, the extent of a reaction of an analyte with a reactant in an assay domain or the amount of an analyte of interest immobilized on a binding domain correlates with the concentration of the analyte in the liquid fraction of the sample (e.g., the plasma concentration in a whole blood sample) but is substantially independent of the volume fraction of the sample occupied by particulate material (e.g., the hematocrit of a whole blood sample). Likewise, the reaction and/or binding of a second analyte at a second domain correlates with the concentration of the second analyte in the liquid fraction of the sample. Accordingly, the methods may further comprise the act of determining a measurement of the concentration of a plurality of analytes in the liquid fraction of the sample that equals or closely approximates the actual concentration of the analytes in the liquid fraction of the sample (i.e. as would be measured for a sample consisting of the pure liquid fraction from which essentially all particulate matter was removed prior to the measurement). In certain embodiments, this act does not include applying a hematocrit correction. According to one embodiment of the invention, i) the extent of the reaction of analytes in a whole blood sample with reactants on assay domains and/or ii) the amount of analytes immobilized on binding domains from a whole blood sample is hematocrit independent and the measurement of these reactions or bindings (or the assay signal resulting from these reactions or bindings) is indicative of the analyte concentrations in the plasma fraction.

Analytes that may be measured using the methods of the invention include, but are not limited to, proteins, toxins, nucleic acids, microorganisms, viruses, cells, fungi, spores, carbohydrates, lipids, glycoproteins, lipoproteins, polysaccharides, drugs, hormones, steroids and any modified derivative of the above molecules, or any complex comprising one or more of the above molecules or combinations thereof. The analytes of interest may be indicative of a disease or disease condition.

Another embodiment of the present invention provides a method for obtaining a measurement indicative of the concentration of one or more, e.g., two or more analytes in a plasma fraction of a whole blood sample. Two or more analytes may be measured in the same sample. Panels of analytes that can be measured in the same sample include for example panels of assays for analytes or activities associated with a disease state or physiological conditions. Certain such panels include panels of cytokines and/or their receptors (e.g., one or more of TNF-$\alpha$, TNF-$\beta$, IL1-$\alpha$, IL1-$\beta$, IL2, IL4, IL6, IL10, IL12, IFN-$\gamma$, etc.), growth factors and/or their receptors (e.g., one or more of EGF, VGF, TGF, VEGF, etc.), drugs of abuse, therapeutic drugs, auto-antibodies (e.g., one or more antibodies directed against the Sm, RNP, SS-A, SS-B Jo-1, and Scl-70 antigens), allergen specific antibodies, tumor markers (e.g., one or more of CEA, PSA, CA 125 II, CA 15-3, CA 19-9, CA 72-4, CYFRA 21-1, NSE, AFP, etc.), markers of cardiac disease including congestive heart disease and/or acute myocardial infarction (e.g., one or more of Troponin T, Troponin I, myoglobin, CKMB, myeloperoxidase, glutathione peroxidase, $\beta$-natriuretic protein (BNP), $\alpha$-natriuretic protein (ANP), endothelin, aldosterone, C-reactive protein (CRP), etc.), markers associated with hemostasis (e.g., one or more of Fibrin monomer, D-dimer, thrombin-antithrombin complex, prothrombin fragments 1 & 2, anti-Factor Xa, etc.), markers of acute viral hepatitis infection (e.g., one or more of IgM antibody to hepatitis A virus, IgM antibody to hepatitis B core antigen, hepatitis B surface antigen, antibody to hepatitis C virus, etc.), markers of Alzheimers Disease ($\beta$-amyloid, tau-protein, etc.), markers of osteoporosis (e.g., one or more of cross-linked N or C-telopeptides, total deoxypyridinoline, free deoxypyridinoline, osteocalcin, alkaline phosphatase, C-terminal propeptide of type I collagen, bone-specific alkaline phosphatase, etc.), markers of fertility state or fertility associated disorders (e.g., one or more of Estradiol, progesterone, follicle stimulating hormone (FSH), luetenizing hormone (LH), prolactin, $\beta$-hCG, testosterone, etc.), markers of thyroid disorders (e.g., one or more of thyroid stimulating hormone (TSH), Total T3, Free T3, Total T4, Free T4, and reverse T3), and markers of prostrate cancer (e.g., one or more of total PSA, free PSA, complexed PSA, prostatic acid phosphatase, creatine kinase, etc.). Certain embodiments of invention include measuring, e.g., one or more, two or more, four or more or 10 or more analytes associated with a specific disease state or physiological condition (e.g., analytes grouped together in the panels listed above).

The binding assays of the invention may employ antibodies as binding reagents. Other suitable binding reagents for use with the methods of certain embodiments of the invention include, but are not limited to, receptors, ligands, haptens, antigens, epitopes, mimitopes, aptamers, hybridization partners, and intercalaters. Suitable binding reagent compositions include, but are not limited to, proteins, nucleic acids, drugs, steroids, hormones, lipids, polysaccharides, and combinations thereof. The term "antibody" includes intact antibody molecules (including hybrid antibodies assembled by in vitro re-association of antibody subunits), antibody fragments and recombinant protein constructs comprising an antigen binding domain of an antibody (as described, e.g., in Porter, R. R. and Weir, R. C. *J. Cell Physiol.,* 67 (Suppl 1); 51-64 (1966) and Hochman, J. Inbar, D. and Givol, D. *Biochemistry* 12: 1130 (1973)). The term "antibody" also includes intact antibody molecules, antibody fragments and antibody constructs that have been chemically modified, e.g., by the introduction of a label.

One of ordinary skill in the art will be able to readily select detection technologies suitable for use with the methods of the invention. These detection technologies include, but are not limited to, a variety of methods that are currently available for measuring reactions (e.g., for measuring enzymatic reactions or binding reactions). Some techniques allow for measurements to be made by visual inspection, others may require or benefit from the use of an instrument to conduct the measurement. Techniques for measuring analytes may include coupling a reaction of the analyte (e.g., an enzyme catalyzed reaction) to a change in optical absorbance, fluorescence, chemiluminescence, electrical current, electrical potential, etc. Techniques available for measuring binding assays include solid phase binding assay techniques in which binding reaction products are formed on a surface and homogenous binding assay techniques in which binding reaction products remain in solution. Suitable detection techniques may detect binding events by measuring the participation of labeled binding reagents through the measurement of the labels via their photoluminescence (e.g., via measurement of fluorescence, time-resolved fluoresecence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

An immunoassay or other type of specific binding assay according to certain embodiments of the invention can involve a number of formats available in the art including solid phase binding assay formats. The antibodies and/or other types of specific binding partners can be labeled with a label or immobilized on a surface. Suitable surfaces include, but are not limited to, glass, ceramic, polymer, polymer composite, and metal surfaces. A variety of different textured surfaces may be used including flat surfaces and rough surfaces. In one embodiment, the surface is an electrode surface, e.g., an electrode surface within a multi-well plate, a flow cell or a flow cell chamber of a cartridge. Surfaces that are rough and/or suitable for use as electrodes may be provided for by using a surface that comprises a material comprising elemental carbon, for example, a composite material containing particulate carbon in a matrix, e.g., a carbon ink.

In embodiments of the invention that employ a solid phase binding assay format, the method, may comprise binding an analyte in a sample to a binding reagent (the capture reagent) immobilized on a binding surface (e.g., by contacting at least a portion of the sample with the surface) and measuring the amount of analyte bound to the surface. "Binding," as used herein, may refer to a direct interaction between a binding reagent and an analyte (e.g., the binding of an analyte to an immobilized anti-analyte antibody) or may involve an indirect interaction through one or more intermediate species (e.g., the binding to immobilized streptavidin of a complex comprising an analyte bound to a biotin-labeled anti-analyte antibody). These intermediate species may be referred to herein as "bridging" species. Multiplexed assays may be carried out in an analogous fashion by employing a plurality of binding domains comprising capture reagents, the binding domains differing in their selectivity for analytes of interest. By way of example, a multiplexed method may comprise contacting a sample with a plurality of binding domains on one or more surfaces, binding a first analyte to a first of the plurality of domains, binding a second analyte to a second of the plurality of domains and measuring the amount of the first analyte on the first domain and the second analyte on the second domain.

The solid phase binding assay may employ a sandwich binding assay format. Such a method may comprise binding an analyte in a sample to a binding reagent (the capture reagent) immobilized on a binding surface, binding the analyte to another binding reagent (the detection reagent) comprising a detectable label and measuring the amount of the detectable label on the binding surface. The assay may be carried out under conditions that allow both the first and second binding reagents to bind to the analyte to form a "sandwich" complex. Examples of sandwich immunoassays performed on test strips are described in U.S. Pat. No. 4,168, 146 to Grubb et al. and U.S. Pat. No. 4,366,241 to Tom et al., both of which are incorporated herein by reference. Multiplexed assays may be carried out in an analogous fashion by employing a plurality of binding domains, on one or more surfaces, comprising capture reagents, the binding domains differing in their selectivity for analytes of interest. One or more detection reagents may be used, as necessary, to bind to the different analytes of interest. By way of example, a multiplexed assay may comprise contacting at least a portion of a sample with a plurality of binding domains on one or more surfaces, binding a first analyte to a first of the plurality of domains, binding a second analyte to a second of the plurality of domains, binding the first and second analytes to one or more labeled detection reagents and measuring the amount of label on the first domain and second domains.

The solid phase binding assay may employ a competitive binding assay format. One such method comprises a) competitively binding to a binding reagent (the capture reagent) immobilized on a binding surface i) an analyte in a sample and ii) a labeled analog of the analyte comprising a detectable label (the detection reagent) and b) measuring the amount of the label on the binding surface. Another such method comprises a) competitively binding to a binding reagent having a detectable label (the detection reagent) i) an analyte in a sample and ii) an analog of the analyte that is immobilized on a binding surface (the capture reagent) and b) measuring the amount of the label on the binding surface. An "analog of an analyte" refers, herein, to a species that competes with the analyte for binding to a binding reagent. Examples of competitive immunoassays are disclosed in U.S. Pat. No. 4,235, 601 to Deutsch et al., U.S. Pat. No. 4,442,204 to Liotta, and U.S. Pat. No. 5,208,535 to Buechler et al., all of which are incorporated herein by reference. Multiplexed assays may be carried out in an analogous fashion by employing a plurality of binding domains, on one or more surfaces, comprising capture reagents, the binding domains differing in their selectivity for binding or competing with analytes of interest. One or more detection reagents may be used, as necessary, to bind or compete with the different analytes of interest. By way of example, a multiplexed assay may comprise contacting a sample with a plurality of binding domains on one or more surfaces and contacting the binding domains with one or more labeled detection reagents, wherein the binding of a first detection reagent to a first binding domain is competitively inhibited by a first analyte and the binding of a second detection reagent to a second binding domain is competitively inhibited by a second detection reagent.

By appropriate selection of capture and detection antibodies, multiplexed solid phase binding assays may be carried out that include both sandwich binding assays and competitive binding assays.

The solid phase binding methods of certain embodiments of the present invention may further comprise displacing (e.g., washing or otherwise removing) sample from a binding surface prior to measuring the amount of bound analyte. Displacement may be effected, e.g., by washing the surface with a wash reagent or by displacing sample material with air. In some embodiments of the invention that include a displacement act, the surface is, concurrently or subsequent to the displacement act, contacted with a detection reagent. By way of example, in one embodiment of a sandwich binding assay that includes a displacement act, at least a portion of a sample is contacted with a binding surface so as to capture analyte on the surface, the sample is removed, and the surface is contacted with a labeled binding reagent that binds to captured analyte and forms the sandwich complex. In one embodiment of a competitive assay that includes a displacement act, at least a portion of a sample is contacted with a binding surface so as to capture analyte on the surface, the sample is removed, and the surface is contacted with a labeled analog of the analyte that binds to unoccupied binding sites on the surface. The detection reagents may be present in a wash reagent used to displace sample material. Alternatively, the detection reagents may be added subsequent to the displacement of sample.

The measurement of analytes in the liquid fraction of a sample may be carried out using assay reagents supported on rough surfaces. The roughness characteristics of the surfaces in such embodiments may be selected so that the surface structure prevents particles in a sample from contacting much of the surface while providing less of a barrier to analytes and, optionally, soluble reagents that participate in the assay (such as detection binding reagents, e.g., detection antibodies). In one embodiment, the ratio of the surface area accessible to an analyte and/or soluble reagent relative to the surface area accessible to a particle in the sample is greater than two. In other embodiments, this ratio is greater than four, ten or fifty. In specific embodiments useful in whole blood assays, the surface may be selected to provide a barrier to red blood cells but not to analyte and/or soluble reagents. By way of example, the surface may be selected so that the ratio of the surface area accessible to IgG molecules is two, four, ten or fifty times greater than the surface area accessible to red blood cells. The surface may be the surface of an inherently rough material or, alternatively, a rough surface may be produced using, e.g., manufacturing techniques known in the art such as etching, micromolding, micromachining, electroforming, chemical vapor deposition, photolithography, etc. The surface may be formed from a composite material comprising particles distributed in a matrix, the exposed particles on the surface of the material providing the desired roughness characteristics. Suitable materials include composites comprising carbon particles such as amorphous carbon particles, graphitic particles and carbon nanotubes. Optionally, the composite may be etched (e.g., by chemical or plasma etching) to expose more particles and increase the surface roughness. In one specific example, the surface is provided by a printed carbon ink.

According to another embodiment of the invention, the measurement of analytes in the liquid fraction of a sample (e.g., in the plasma fraction of a whole blood sample) is conducted under conditions in which there is no substantial depletion of analyte from the sample. The measurement may involve an assay reaction that reaches equilibrium without substantially depleting analyte from the sample. For example the amount and binding affinity of binding reagents in one or more binding domains may be chosen so that the binding of analytes in a sample to these binding domains reaches equilibrium without binding more than 30% of any analyte (no more than 10%, no more than 20%, or, no more than 1%) to the corresponding binding domain. In one embodiment the amount of a binding reagent (in moles) present in a binding domain contacted with a volume of sample is not more than 0.1 V/K where V is the volume of sample (in liters) and K is the affinity constant for the binding of the binding reagent to analyte (in liters/mol).

According to another embodiment, the assay may be conducted without significant depletion of analyte by carrying out the assay in a kinetic regime, i.e., by carrying out the assay reactions for a period of time which may be a predetermined period of time) that is shorter than the time required for the reaction to reach equilibrium. This time may be selected so that no more than 30%, 20%, 10% or 1% of an analyte is depleted from the sample, e.g., by binding of the analyte to a binding domain. The time in certain embodiments is less than 15 minutes, less than 10 minutes, less than 5 minutes or less than 3 minutes. In one embodiment, at least a portion of a sample is contacted with a surface, for example, with a surface containing a first binding partner of an analyte of interest immobilized thereon, for a defined interval of time shorter than the interval of time required to reach an equilibrium between the analyte immobilized on the surface and free in solution, in certain embodiments for a period of time shorter than 15 minutes, shorter than 10 minutes, shorter than 5 minutes, or shorter or equal to three minutes.

According to another embodiment, measurement of analytes in the liquid fraction of a sample (e.g., the plasma fraction of whole blood) is carried out in a solid phase assay format by flowing the sample over an assay surface, e.g., a surface with one or more binding domains. In certain embodiments, the flow is carried out under conditions that improve mass transport of analyte to the assay surface or assay domains defined thereon. The sample may be passed over the surface under conditions of continuous flow. Alternatively, the sample may be moved back and forth over the surface (reciprocal flow) to increase the contact time between a volume of sample and the assay surface. During periods of flow, the flow may be turbulent or laminar. The flow rate in certain embodiments is selected to provide substantially laminar flow. The laminar nature of the flow can be characterized by the Reynold's number of the flow. The Reynold's number for the flow may be less than 100 or less than 10. In one specific embodiment, the assay surfaces used in a solid phase assays of the invention define, at least in part, the interior surfaces of a flow cell through which the sample is passed. The flow rates and flow cell dimensions may be chosen so as to provide laminar flow of sample through the flow cell. In certain embodiments, analyte is not substantially depleted from the sample during the assay.

According to another embodiment, the flow of sample over an assay surface is controlled so as to focus the flow of particulates into flow paths which minimize contact of the particulates with the surface, thus providing a layer of low-particulate liquid over the surface. In one example, the flow conditions are selected to provide laminar flow over the assay surface with the particulates in the sample restricted to faster moving laminae of the flow-removed from the surface and, e.g., located towards the middle of the flow path of sample through a flow cell (FIG. 1). In the case of blood samples, a plasma-rich layer can, therefore, be maintained directly adjacent the assay surface. Without being restricted to any particular physical theory or explanation, although blood is a non-Newtonian fluid, it is believed that under flow and high shear rates the red blood cells tend to separate from aggregates, common at quiescent conditions, and align with the flow as a result of cell stretching or deforming. (Boryczko K., et al., (2003) *J. Mol. Model.,* 9:16-33; Pries, A. R, et. al. (1992) *Am. J. Physiol. Heart Circ. Physiol.* 263: H1770-H1778). This alignment also causes the blood cells to move in layers sliding past clear layers of plasma. In certain embodiments, analyte is not substantially depleted from the sample during the assay.

For embodiments wherein a flowing fluid is involved, the fluid flow is, optionally, carried out under conditions that provide a flow rate that is independent of viscosity for the range of samples that may be analyzed. By way of example, a sample may be pumped (e.g., by application of pressure or vacuum to the sample or electro-osmotic flow, etc.) through a cell or conduit (which may be a flow cell with assay surfaces or a separate conduit), the flow rate through the conduit may be measured (e.g., through the use of capacitance, optical or conductometric sensors to measure the time the sample takes to move a defined distance through the cell or conduit) and the pressure or vacuum may be adjusted to adjust the flow rate to a predetermined desired value.

According to another embodiment, measurement of analytes in the liquid fraction of a sample (e.g., the plasma fraction of whole blood) is carried out in a solid phase assay format by introducing the sample into an assay cell (e.g., by flowing the sample into a flow cell or introducing the sample into an assay tube, etc.). The assay cell can comprise one or more assay surfaces (e.g., surface with one or more binding domains or other type of assay domains), the surfaces being arranged within the assay cell such that they face sidewise or downwards during operation of the cell. By way of example, the binding surface may define, at least in part, the top surface an internal chamber of the assay cell. The sample may be introduced into the assay cell and held in the cell under conditions which allow particles in the sample to settle (e.g., under no flow or low flow conditions) away from the assay surface(s) and thus provide a plasma-rich layer near the assay surface(s). The method may further comprise, after the settling has occurred, flowing the sample past the assay surface(s) under laminar flow (optionally, in a back and forth movement) so as to introduce convectional mixing while maintaining a plasma-rich layer near the assay surface(s). In certain embodiments, analyte is not substantially depleted from the sample during the assay.

The solid phase binding methods of the present invention may further comprise displacing the whole blood sample, for example, displacing by introducing an assay buffer or a wash solution onto the surface, in certain embodiments with an assay buffer or a wash solution containing a second binding reagent, for example, a second binding reagent labeled with a label, prior to measuring or prior to generating an assay signal. Certain methods may further comprise an act of contacting a surface with a second binding reagent, for example, with a second binding reagent labeled with a label, or, in certain embodiments, labeled with an ECL label after the whole blood sample was displaced from a surface.

Certain methods of the invention may, advantageously, be used to perform rapid blood tests and may be especially suited to carrying out tests in point-of-care settings, in particular at point-of-care settings where users may not be trained to use or have access to equipment for separating plasma or serum from blood or where the available blood samples (e.g., finger prick samples) are too small in volume for convenient preparation of plasma or serum. In one embodiment, the invention is a method for performing a rapid blood test, for example at a point-of-care setting, which can be completed within 30 minutes, (within 20 minutes, or within 10 minutes) comprising:

a) drawing a sample of blood from a patient to provide a whole blood sample;

b) applying the whole blood sample to an assay module (for example, an assay plate or an assay cartridge) comprising a binding surface;

c) flowing the whole blood sample over the surface for a defined interval of time to immobilize an amount of an analyte of interest on a surface; and d) measuring an amount of an analyte on a surface, for example, by measuring an amount of a label on a surface;

e) determining a measure of the concentration of the analyte in blood plasma, for example by using a calibrator;

wherein the amount of analyte immobilized on a surface is substantially independent of the hematocrit of the whole blood sample and the determining act is conducted without hematocrit correction.

Advantageously, certain methods of the present invention can be performed by users with minimal training requirements.

The assay surfaces or domains used in certain assay methods of the invention may be comprised in assay modules (e.g., assay cartridges, assay plates, etc.) having one or more assay cells (e.g., wells, compartments, chambers, conduits, flow cells, etc.). One embodiment of the invention employs an assay module with an assay surface having an array of assay domains. In one specific example of this embodiment, the array is a two dimensional array. In another specific example, the array is a one dimensional array that is aligned along the flow path of a flow cell in an assay cartridge.

Assay domains may be supported on a variety of different assay surface materials including, but not limited to plastics, ceramics, metals, glasses, composites and the like. In embodiments that employ electrochemical or electrode induced luminescence measurements (such as electrochemiluminescence measurements), the assay surfaces may be chosen and configured so as to be capable of acting as electrodes. Surfaces suitable for use as electrodes include surfaces comprising materials comprising elemental carbon, for example, a composite material containing particulate carbon in a matrix, e.g., a carbon ink. The assay modules may also include additional electrode surfaces to provide counter or reference electrodes. Assay modules, and in particular assay cartridges and cartridge readers, suitable for use in carrying out electrochemiluminescence based measurements using methods of the invention are described in detail in U.S. patent application Ser. No. 10/744,726, now issued as U.S. Pat. No. 7,497,997, hereby incorporated by reference.

One embodiment of the invention employs a cartridge that includes one or more sample chambers, one or more detection chambers (e.g., detection chambers adapted for use in ECL measurements as described below) and one or more waste chambers for holding liquid wastes. The chambers are connected in series by fluid conduits so that a sample introduced into a sample chamber can be delivered into one or more detection chambers for analysis and then passed into one or more waste chambers. This cartridge may also include one or more reagent chambers for storing liquid reagents, the reagent chambers connected via conduits to the other components so as to allow the introduction of the liquid reagents into specified sample or detection chambers. The cartridge may also include vent ports in fluidic communication with the sample, detection and/or waste chambers (directly or through vent conduits) so as to allow the equilibration of fluid in the chambers with the atmosphere or to allow for the directed movement of fluid into or out of a specified chamber, e.g. in or out waste chambers to the detection chamber, by the application of positive or negative pressure.

The detection chambers may be adapted for carrying out a physical measurement on the sample. The detection chamber may be connected to an inlet conduit. In certain embodiments, the detection chamber is also connected to an outlet conduit and is arranged as a flow cell. In certain embodiments, the flow along the flow cell during its operation is substantially laminar, with Reynolds numbers less than 1000, less than a 100, less than 10 and in certain embodiments less than 5. If the measurement requires illumination or optical observation of the sample (e.g., as in measurements of light absorbance, photoluminescence, reflectance, chemiluminescence, electrochemiluminescence, light scattering and the like) the detection chamber may have at least one transparent wall arranged so as to allow the illumination and/or observation. When employed in solid phase binding assays, the detection chamber may comprise a surface (e.g., a wall of the chamber) that has one or more binding reagents (e.g., antibodies, proteins, receptors, ligands, haptens, nucleic acids, etc.) immobilized thereon (e.g., an array of immobilized binding reagents, such as an array of immobilized antibodies and/or nucleic acids). In one such embodiment, the array is a one-dimensional array aligned along the flow path of a flow cell. In another such embodiment, at least two of the binding domains formed by the binding reagents differ in specificity for analytes of interest.

In one embodiment, the detection chamber is an electrochemiluminescence detection chamber, which may have one or more binding reagents immobilized on one or more electrodes. In one embodiment, the cartridge comprises a working electrode having an array of binding reagents immobilized thereon. In another embodiment, the cartridge comprises an array of independently controllable working electrodes each having a binding reagent immobilized thereon.

One embodiment of an electrochemiluminescence detection chamber is a chamber having a fluid inlet and fluid outlet and a flow path between the inlet and outlet. An array of electrodes may be patterned on an internal surface of the chamber, for example, in a one dimensional array along the fluid flow path. The internal chamber surface opposing the electrode array may be light-transmissive so as to allow for the detection of light generated at the electrodes. One or more of the electrodes may comprise assay reagents, for example, a first binding reagent, immobilized on the electrode. These assay domains may be used to carry out assay reactions which can be detected by using the electrode to induce an assay dependent signal, such as an electrochemical or, an electrode induced luminescence signal, and detecting the signal. In certain embodiments, these assay reagents are arranged in one or more assay domains defined by apertures in a dielectric layer deposited on the electrode.

The cartridge may comprise additional reagents used in the assay methods, e.g., binding reagents (such as antibodies, nucleic acids, etc. which may be labeled with a detectable label), agents that compete with an analyte for binding to a binding reagent, anticoagulants (e.g., heparin, citrate, oxalate, EDTA, etc.), pH buffering components, salts, blocking agents (e.g., proteins that block non-specific binding and/or block the binding of heterophile antibodies) and preservatives (e.g., fluoride, iodoacetate, etc.). One or more of these reagents may be provided on the cartridge in dry form. Such a cartridge may also provide liquid reagents such as wash buffers, extraction buffers, read buffers (e.g., ECL coreactant containing solutions for ECL-based assays).

An assay cartridge may contain active mechanical or electronic components such as pumps, valves, sensors (e.g., light detectors), sources of electrical power and the like as needed, e.g., to move fluids in the cartridge or to generate and/or detect assay signals. In one embodiment of the invention, an assay cartridge has minimal or no active mechanical or electronic components. When carrying out an assay, such an assay cartridge may be introduced into a cartridge reader which provides these functions. For example, the reader may have pumps, valves, heaters, sensors, etc. for providing fluids to the cartridge, verifying the presence of fluids and/or maintaining the fluids at an appropriate controlled temperature. The reader may be used to store and provide assay reagents, either onboard the reader itself or from separate assay reagent bottles or an assay reagent storage device. In one embodiment of a cartridge reader, the reader moves fluids in a cartridge by applying positive or negative air pressure to ports on the cartridge, in certain cases, without the cartridge reader coming in contact with liquid samples or reagents. The reader may also have sensors, such as capacitive sensors or optical sensors, for monitoring and allowing precise control of fluid movement through the cartridge.

A assay procedure using an assay module and assay reader may comprise inserting the cartridge in the reader, making the appropriate electrical, fluidic and/or optical connections to the cartridge (making use of electrical, fluidic and/or optical connectors on the cartridge and reader), and conducting an assay in the cartridge. A whole blood sample may be introduced into the cartridge prior to inserting the cartridge in the reader. The assay may also involve adding one or more assay reagents to the cartridge; for example, one or more assay reagents, such as binding reagents, are stored in the cartridge in a dry and/or wet form.

FIG. 2 is a schematic representation of cartridge 200, one embodiment of a cartridge of the invention that incorporates many of the fluidic features described above. This exemplary embodiment depicts a cartridge comprising an electrode array of the invention. The skilled artisan, however, can readily adapt the fluidic components and design to cartridges employing other detection chamber designs and/or detection technologies. Cartridge 200 comprises various compartments including a sample chamber 220, assay reagent chamber 225, waste chambers 230 and 231 and detection chambers 245 and 246 comprising electrode arrays 249a and 249b and electrode contacts 297 and 298. Also depicted in FIG. 2 are fluid ports/vents 250-253 and 280 that may be utilized as fluidic control points, vents for allowing a chamber to equilibrate with atmospheric pressure, ports for introducing air bubbles or slugs into a fluid stream and/or as fluidic connections to a cartridge reader. FIG. 2 also depicts a number of fluidic conduits (shown as lines connecting the various chambers) that establish a fluidic network that connects the various compartments and/or fluid ports/vents. The fluidic conduits may comprise distribution points to distribute a fluid to two or more locations/compartments in a cartridge and sharp angles that prevent passive fluid flow (ensuring that fluid movement past these features only occurs during active movement of the fluids). Other fluidic features that are shown in FIG. 2 include pill chambers/zones 290, 291 for each of the read chambers.

Sample chamber 220 is a chamber defined within cartridge 200 that is adapted for receiving a sample, for example a liquid sample, to be analyzed in the cartridge. Cartridge 200 may also include a sealable closure for sealing sample introduction port 221. Reagent chamber 225 is a chamber adapted to hold a liquid reagent and includes a vent conduit linked to vent port 250 and reagent conduit linked to the sample conduit. Pill chambers/zones 290 and 291 hold dry reagents and are positioned, respectively, in the fluidic pathway between sample port 220 and detection chambers 245 and 246 so that liquid passing through the chamber/zones will reconstitute the dried reagents and carry the resulting solutions into the detection chambers. Reagent chamber 225, vent port 280 and/or pill chamber zones 290 and/or 291 may optionally be omitted.

Detection chambers 245 and 246 are adapted for carrying out electrochemiluminescence-assays and comprise arrays of electrodes 249a and 249b having binding domains 248a and 248b comprising immobilized binding reagents. During operation, the cartridge may be held (e.g., by a cartridge reader) so that the surface having the binding domains faces substantially upward, downward or sideways. Optionally, detection chamber 246 is omitted. Detection chambers 245 and 246 are connected via waste conduits to waste chambers 231 and 230. Waste chambers 230 and 231 are chambers configured to hold excess or waste fluids and are also connected, respectively, to vent port 252 via a vent conduit and vent port 251 via a vent conduit. The use of multiple waste chambers advantageously allows fluid flow through the multiple chambers to be controlled independently via the application of vacuum or pressure to the waste chamber vent ports. Alternatively, only one waste chamber is used (e.g., waste chamber 230 is omitted and detection chambers 245 and 246 are both connected to waste chamber 231).

Figure 3A:
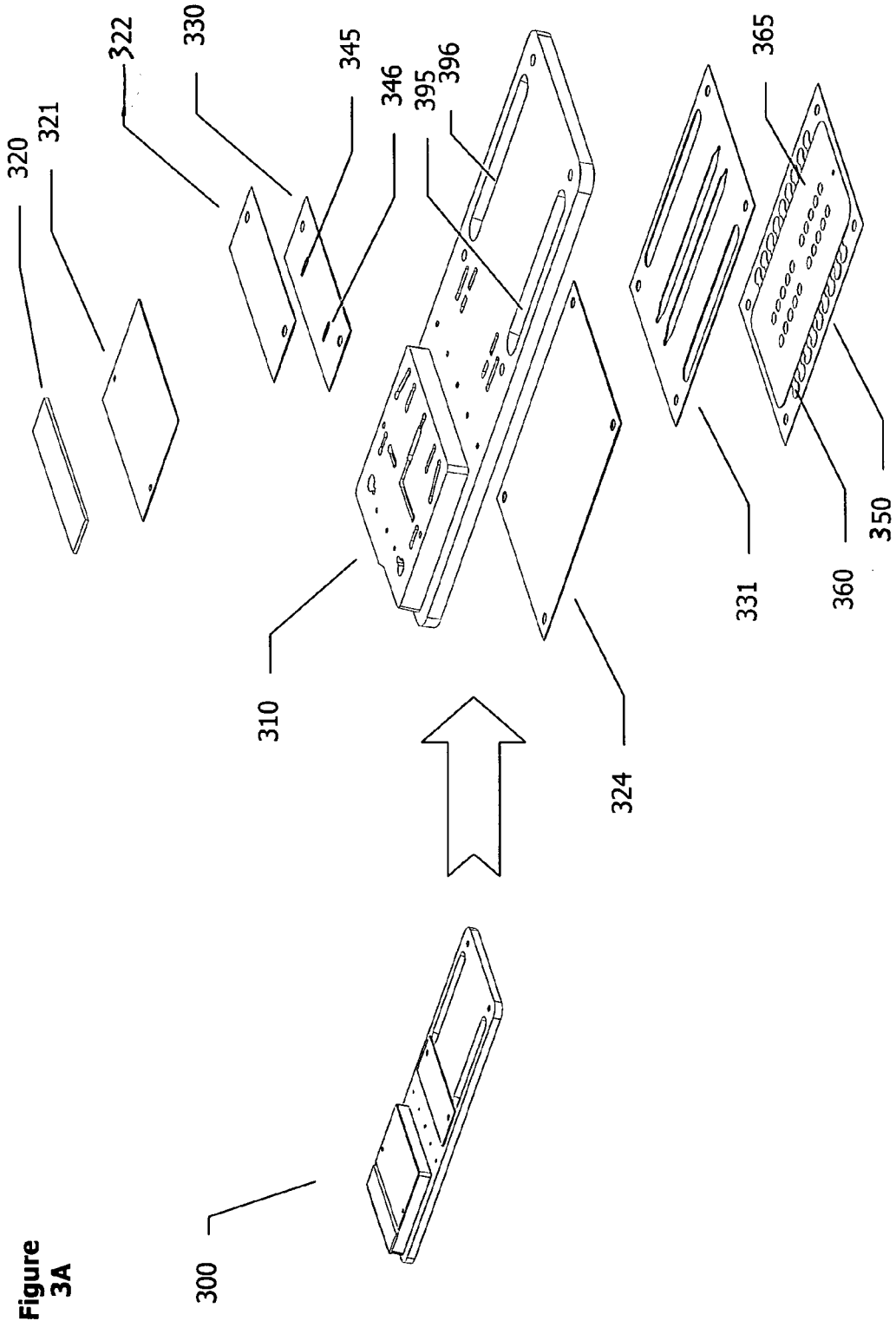
FIG. 3A shows an exploded view of a cartridge according to one embodiment.
Figure 3B:
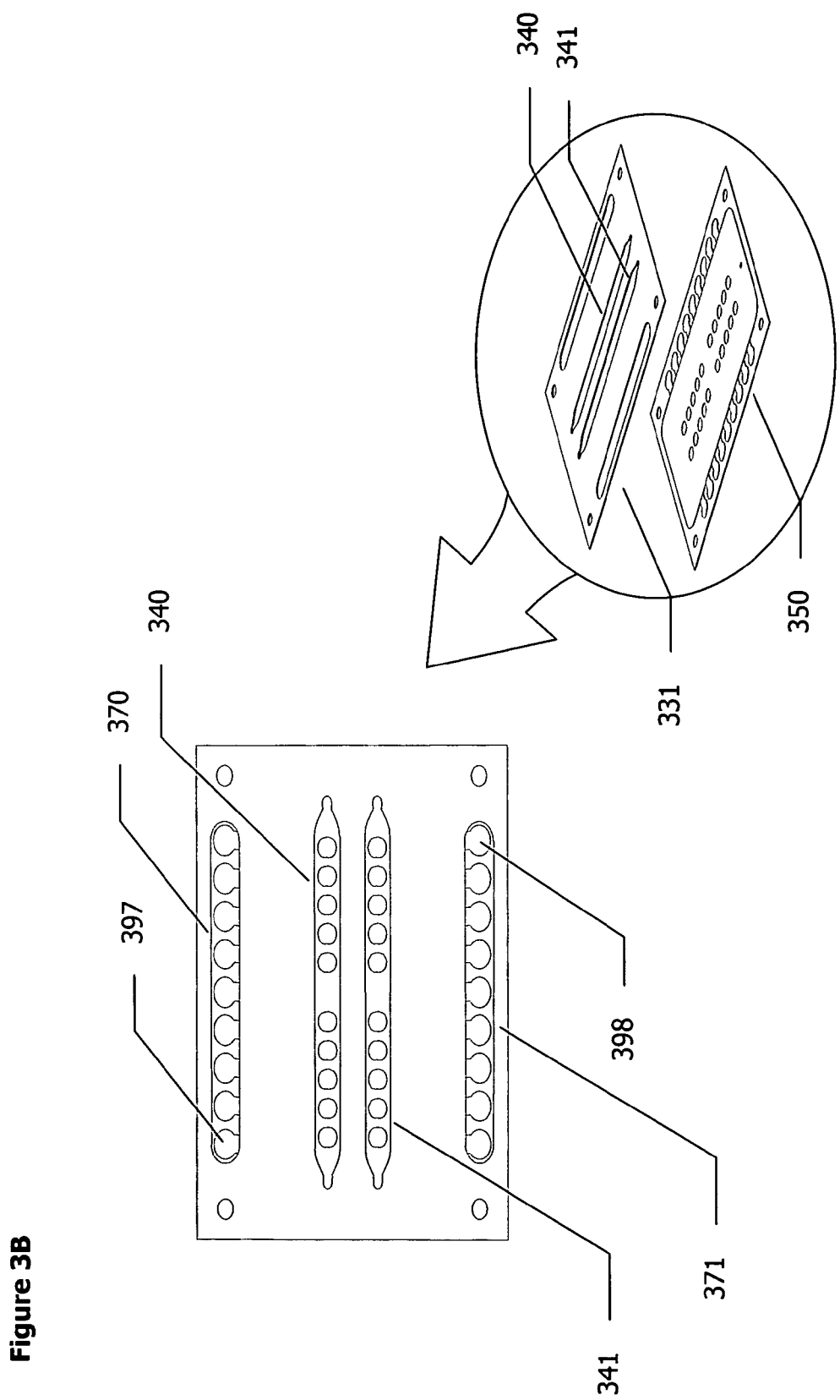
FIG. 3B shows a detailed view of the alignment of two components of the cartridge of FIG. 3A.

FIG. 3A shows an exploded view of cartridge 300, one implementation of cartridge 200 that comprises cartridge body 310 and cover layers 324, 350, 320, 321 and 322 mated to the surfaces of cartridge body 310 either directly or through gasket layers such as gasket layers 330 and 331. Cartridge body 310 includes features (channels, grooves, wells, compartments, etc.) and may be prepared by injection molding of a plastic. The features are sealed to provide some of the chambers and conduits of the cartridge by applying the cover layers to the upper and lower portions of the cartridge body (either directly or through an intervening gasket layer). Specifically, detection chambers (such as detection chambers 245 and 246 in FIG. 2) are formed by sealing cover layer 350 (having patterned conductive layer 360 (which forms the patterned electrode array 249a and 249b, shown in FIG. 2) and patterned dielectric overlayer 365) to cartridge body 310 through intervening gasket layer 331 made in certain embodiments, from double sided adhesive tape). FIG. 3B shows the alignment of gasket layer 331 with cover layer 350. The detection chamber's depth, length and width are defined by cutouts 340 and 341 within the gasket layer. Holes in patterned conductive layer 360 define an array of exposed electrode surfaces in the detection chambers on which binding reagents are immobilized so as to form one-dimensional arrays of binding domains in the detection chambers.

In the embodiment shown in FIG. 3, the cartridge body further includes electrical access regions 395 and 396 that, together with cutouts 370 and 371 in gasket layer 331 allow electrical contact to be made with electrode contacts 397, 398. Electrical access regions are cut-outs or holes in the cartridge body configured and arranged to be in alignment with the electrode contacts.

Certain features of invention are further illustrated by the following examples.

EXAMPLES

The following examples are illustrative of some of the methods and instrumentation falling within the scope of the present invention. They are, of course, not to be considered in any way limitative of the invention. Numerous changes and modifications can be made with respect to the invention by one of ordinary skill in the art without undue experimentation.

Materials & Methods:

Pooled Cardiac Marker Stock Solution:

A pooled cardiac marker stock solution was prepared that contained myoglobin, cardiac troponin I (TnI), CKMB, and cardiac troponin T (TnT) at 2547, 28.8, 225.5 and 39.4 ng/ml, respectively. Calibration standards were prepared by diluting the pooled cardiac marker stock solution with off-the-clot pooled human serum (Western States Plasma #HS-300) containing the additives 0.1% w/v 2-chloracetamide, 0.01% w/v 2-methyl-4-isothiazolin-3-one, 2.0% w/v sucrose, 0.23% w/v tetrasodium EDTA, 0.16% w/v N-acetyl-L-cysteine, and 0.085% w/v potassium ADP.

Spiked Blood Samples:

In several of the examples described below, a number of whole blood samples were prepared that differed in hematocrit value but had equivalent concentrations of cardiac markers in their respective plasma fractions. That strategy used to make these test samples is illustrated in procedure described below.

Whole blood samples containing lithium heparin as an anticoagulant were obtained from the Research Sample Bank (Pompano Beach, Fla.) and determined to be free of red blood cell lysis before use. A spiked whole blood standard containing added cardiac markers was prepared by combining 9500 ul of the whole blood (39.7% hematocrit) with 500 ul of the pooled cardiac marker stock solution and 100 ul of a solution containing blocking agents (50 mg/mL bovine serum albumin and 5 mg/mL bovine IgG). The spiked blood standard (final hematocrit level of 37%) was mixed for 50 minutes in a gentle orbital motion on an Oxis Instruments Nutator (Ivyland, Pa.). The spiked blood standard was used to prepare additional whole blood samples having the same plasma levels of the cardiac markers but different hematocrit levels.

To prepare a spiked sample with a hematocrit level of 56%, 1.500 mL of the spiked blood standard was spun gently on a StatSpin-RX (Norwood, Mass.) mini-centrifuge plasma separator and 0.500 mL plasma was removed. To prepare a spiked sample with hematocrit level of 47%, 1.500 mL of the spiked blood standard was spun gently and 0.300 mL plasma was removed. To prepare a spiked sample with a hematocrit level of 28%, 0.75 mL of spiked blood standard was combined with 0.25 mL of plasma prepared by centrifuging a separate aliquot of spiked blood standard. To prepare hematocrit level of 19%, 0.75 mL of spiked blood standard was combined with 0.75 mL of plasma prepared by centrifuging a separate aliquot of spiked blood standard. Finally, blood plasma prepared by centrifuging the spiked blood standard was used for a 0 hematocrit sample.

All the spiked samples were mixed in a gentle orbital motion on an Oxis Instruments Nutator (Ivyland, Pa.) for 10 minutes at room temperature before use.

Cardiac Marker Antibodies:

Capture antibodies for myoglobin, TnT, CKMB, and TnI were biotinylated with biotin-LC-sulfo-NHS-ester (BioVeris Inc., Gaithersburg, Md.). Detection antibodies for the same analytes were labeled with Sulfo-TAG NHS Ester (Meso Scale Discovery, Gaithersburg, Md.), an electrochemiluminescent label based on a sulfonated derivative of ruthenium-tris-bipyridine (compound 1 pictured below). Labeled antibodies were purified by size exclusion chromatography on Sephadex G-25 or G-50 (Pharmacia Biosciences).

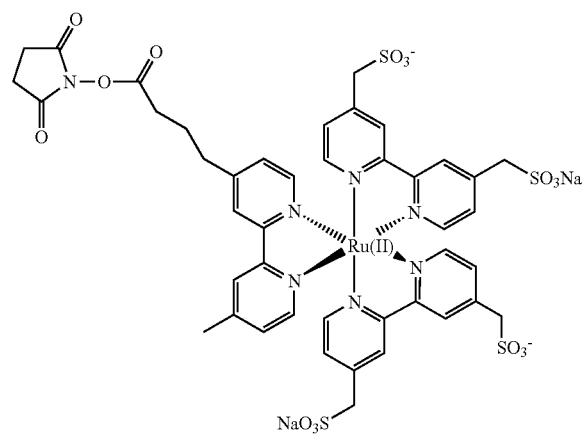

1

Cartridge Assays:

The assays were conducted using assay cartridges as shown in FIG. 3 and as described in more detail in U.S. Pat. No. 7,497,997. Cover layer 350 was provided by a sheet of mylar having a layer of carbon ink forming electrode arrays 360 screen printed thereon and a dielectric layer 365 having apertures that defined the exposed electrode surfaces within the detection chamber. Gasket layer 331 was provided for by double stick tape. The thickness of the double stick tape and the dimensions of the slots were selected so that the detection chambers were 3.175 mm wide and 0.127 mm high and several cm long. Capture antibodies against, myoglobin, TnT, TnI, CKMB and/or progesterone were immobilized on the exposed surfaces so that the surface defined by any one of the apertures had capture antibody directed against only one analyte. The immobilization was carried out by microdispensing solutions containing 60 ug/mL of an antibody on the exposed area (so that it spread to but not past the boundary defined by the dielectric layer), allowing the solution to dry on the electrode, and then blocking any uncoated electrode surface with a BSA solution. Capture antibodies were immobilized in the same pattern in the two detection chambers of the flow cells, allowing each measurement to be carried out in duplicate.

The assays were conducted in one- or two-step formats. Unless noted otherwise, the assays were carried out as described below. The one-step assays were carried out by introducing the sample (premixed with labeled detection reagents for the analytes being measured; antibodies for sandwich assays or analogs of analytes for competitive assays) into the cartridge. By applying vacuum/pressure to and/or venting the appropriate vent ports, sample was introduced into the detection chambers and moved back and forth through the chamber for a period of 4 minutes. The sample was then washed from the detection chamber with a buffered solution containing tripropylamine (MSD Read Buffer T, Meso Scale Diagnostics) and the detection chambers were left filled with the tripropylamine solution. ECL was induced by applying an electrical voltage signal to the electrode contacts (2-5 V over 5 seconds) and the resulting ECL was imaged with a cooled CCD camera. Image analysis software was used to quantitate the ECL emitted from each element of the antibody array.

The two-step assays comprised introducing a sample into the cartridge (in the case of the two-step assay the sample was not premixed with detection reagents), introducing the sample into the detection chambers and moving it back and forth in the chamber for 3 minutes. Washing the sample from the chamber, introducing a solution containing the appropriate detection reagents, and moving this solution back and forth through the chamber for 1 minute. The detection reagents were then washed away with tripropylamine solution and ECL was generated and measured as described for the one-step assay.

Sample and/or detection reagent solutions were moved through the detection chambers at a flow rate of 10 uL/min. For the detection chamber dimensions used and the viscosity and density of the samples, this flow rate corresponds to a Reynold's number for the flow of roughly 3.2.

Example 1

Hematocrit-Independent One-Step Sandwich Immunoassay for Plasma Levels of Cardiac Markers in Whole Blood Samples Six test samples having the same plasma levels of cardiac markers but different hematocrit levels were prepared as described in Materials and Methods. Table 1 provides, for each of the samples, the hematocrit, the concentration of each of the analytes in the blood sample (blood concentration) and the concentration of each of the analytes in the plasma fraction (plasma concentration).

TABLE 1

| Sample | Hematocrit (%) | Blood Concentration (ng/mL) | | | | Plasma Concentration (ng/mL) | | | |
|---|---|---|---|---|---|---|---|---|---|
| | | Myo | TnI | CKMB | TnT | Myo | TnI | CKMB | TnT |
| 1 | 0 | 200 | 2.3 | 18 | 3.1 | 201 | 2.3 | 18 | 3.1 |
| 2 | 19 | 163 | 1.9 | 15 | 2.5 | 201 | 2.3 | 18 | 3.1 |
| 3 | 28 | 145 | 1.7 | 13 | 2.3 | 201 | 2.3 | 18 | 3.1 |
| 4 | 37 | 127 | 1.4 | 11 | 2.2 | 201 | 2.3 | 18 | 3.1 |
| 5 | 47 | 107 | 1.2 | 9.5 | 1.6 | 201 | 2.3 | 18 | 3.1 |
| 6 | 56 | 88 | 1.0 | 7.9 | 1.4 | 201 | 2.3 | 18 | 3.1 |

A solution containing detection antibodies against myoglobin, TnI, CKMB and TnT (3.3 μl) was mixed with 160 μl of each test sample. The final antibody concentrations (in weight per total blood volume) were 2 μg/ml with the exception of the anti-myoglobin antibody, which was 4 μg/ml. The mixtures were incubated for 2 minutes and 150 μl aliquots were transferred into cartridges for measurement. The assays were conducted in one-step format. Two cartridges were used for each hematocrit level giving a total of four replicates per condition (2 per cartridge). The reported signals are normalized by dividing the measured signal by the average signal for the condition that gave the lowest signal for each assay.

Figure 4:
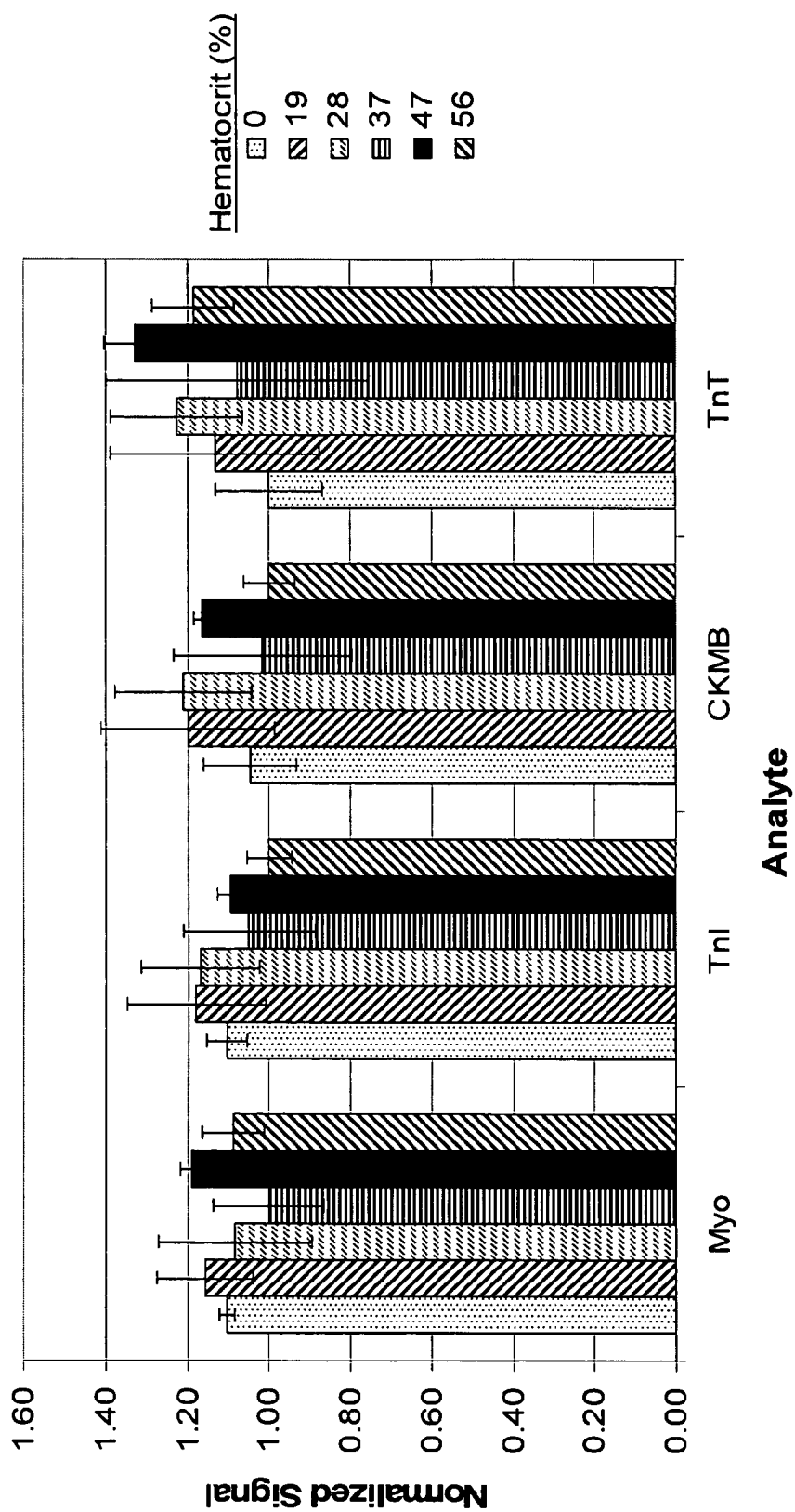
FIG. 4 shows the results of a one-step electrochemiluminescence assay for myoglobin, TnT, CKMB and TnI in whole blood samples. The plot shows ECL signal (vertical axis) for each analyte (horizontal axis) at six hematocrit levels.

FIG. 4 shows the normalized average signal and standard deviation for each condition. The results show no dependence between the ECL signal and the hematocrit level. Samples with equivalent plasma levels of cardiac markers gave roughly equivalent signals despite large differences in the hematocrit and the weight of analyte per volume of whole blood.

Example 2

Hematocrit-Independent One-Step Sandwich Immunoassay for Plasma Levels of Cardiac Markers in Whole Blood Samples Example 1 compared the signals obtained for whole blood samples that varied in hematocrit but contained equal levels of analyte in their plasma fractions. In this example, whole blood samples are analyzed that have equal concentrations of analyte with respect to the total volume of blood. The concentrations of analyte in the plasma should, therefore, vary as a function of the sample hematocrit.

The stock blood sample was prepared by combining 2282 μl of blood (hematocrit level of 42.5%) with 51 μl of a mixture of detection antibodies for myoglobin, cTnT, cTnI, and CKMB at concentrations 193, 97, 163, and 98 μg/ml, respectively and 33 μl of the BSA and bovine IgG blocking agent solution. Whole blood samples at four hematocrit levels were prepared from stock blood sample as described in the Materials and Methods except that the blood stock contained no added analyte. Each of the whole blood samples was spiked with equal amounts of cardiac markers by addition of 26.6 μl of pooled cardiac marker stock solution to 0.5 mL of each hematocrit level. The samples were mixed for 1 hour before testing. Table 2 below lists, for each of the whole blood samples, the hematocrit, the plasma levels of the cardiac markers and the concentration of the markers in the whole blood.

TABLE 2

| Sample | Hematocrit (%) | Blood Concentration (ng/mL) | | | | Plasma Concentration (ng/mL) | | | |
|---|---|---|---|---|---|---|---|---|---|
| | | Myo | TnI | CKMB | TnT | Myo | TnI | CKMB | TnT |
| 1 | 0 | 129 | 1.5 | 11 | 2.0 | 129 | 1.5 | 11 | 2.0 |
| 2 | 20 | 129 | 1.5 | 11 | 2.0 | 161 | 1.8 | 14 | 2.5 |
| 3 | 39 | 129 | 1.5 | 11 | 2.0 | 211 | 2.4 | 19 | 3.3 |
| 4 | 58 | 129 | 1.5 | 11 | 2.0 | 306 | 3.5 | 27 | 4.7 |

Figure 5:
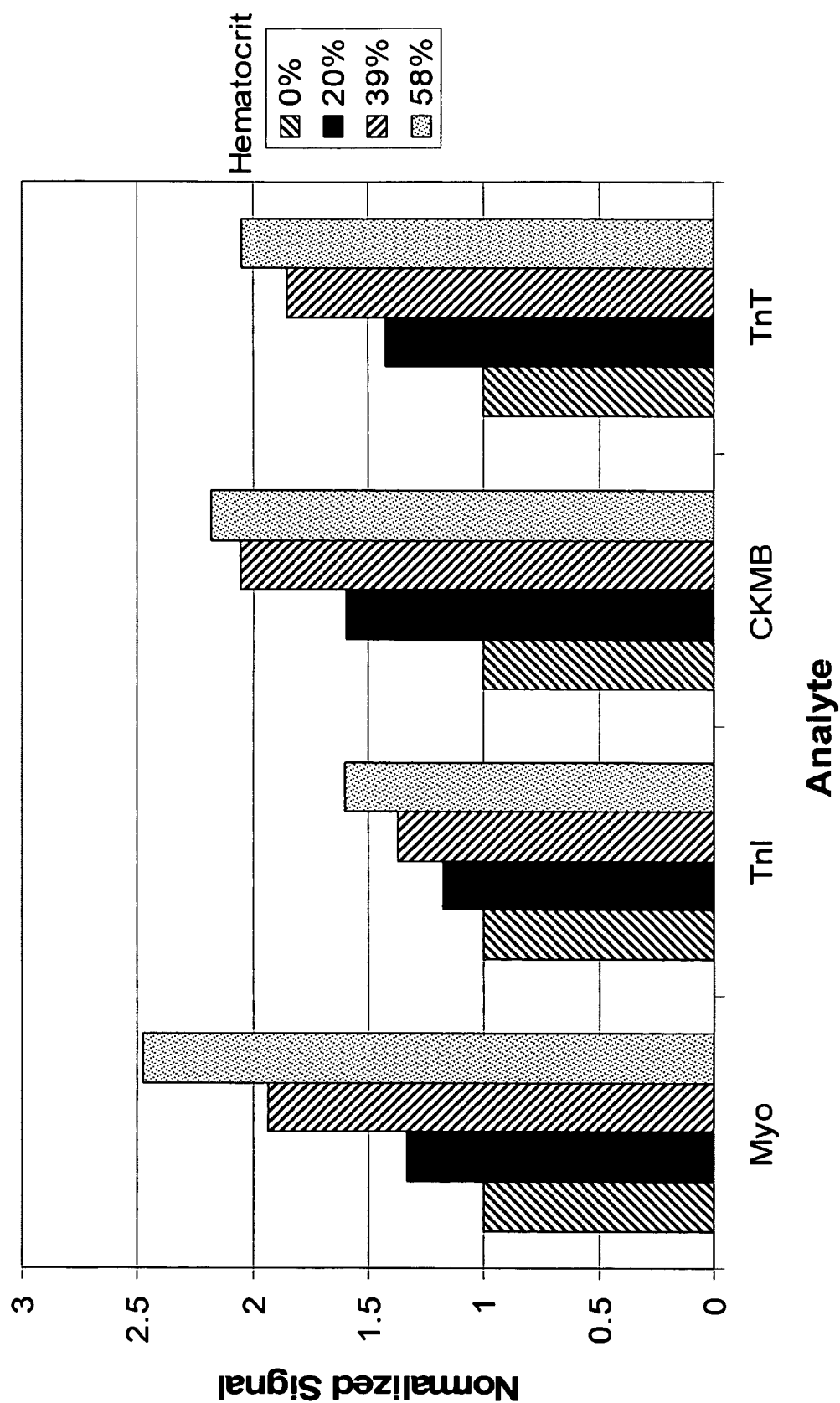
FIG. 5 shows the results of electrochemiluminescence assays for myoglobin, TnT, CKMB and TnI. The plot shows ECL signal (vertical axis) for each analyte (horizontal axis) at various analyte concentrations in blood plasma.

The samples were transferred to cartridges for measurement and analyzed using a one step assay format. FIG. 5 shows the assay signals for each sample (after normalizing by dividing the signal by the signal reported for the zero hematocrit sample). The signal increased with increasing hematocrit confirming that the assay is indicative of analyte levels in the plasma fraction.

Comparative Example 3

One-Step Sandwich Immunoassay for Cardiac Markers in Whole Blood Samples; Incubation Under Static Conditions Whole blood (2800 uL with a hematocrit of 45.7%) was spiked with 112 uL of the pooled cardiac marker solution and 30 uL of a solution containing detection antibodies against myoglobin, CKMB and TnT (giving final antibody concentrations of 14, 3 and 5 ug/mL, respectively) as well as BSA and bovine IgG. Four test samples having the same plasma levels of cardiac markers but different hematocrit levels were prepared from the spiked whole blood by a procedure analogous to that described in the Materials and Methods. The following table 3 provides, for each of the samples, the hematocrit, the concentration of each of the analytes in the blood sample (blood concentration) and the concentration of each of the analytes in the plasma fraction (plasma concentration).

TABLE 3

| Sample | Hematocrit (%) | Blood Concentration (ng/mL) | | | Plasma Concentration (ng/mL) | | |
|---|---|---|---|---|---|---|---|
| | | Myo | CKMB | TnT | Myo | CKMB | TnT |
| 1 | 0 | 170 | 15.1 | 2.6 | 172 | 15 | 2.7 |
| 2 | 21 | 136 | 11.9 | 2.1 | 172 | 15 | 2.7 |
| 3 | 43 | 98 | 8.7 | 1.5 | 172 | 15 | 2.7 |
| 4 | 57 | 74 | 6.5 | 1.1 | 172 | 15 | 2.7 |

Figure 6:
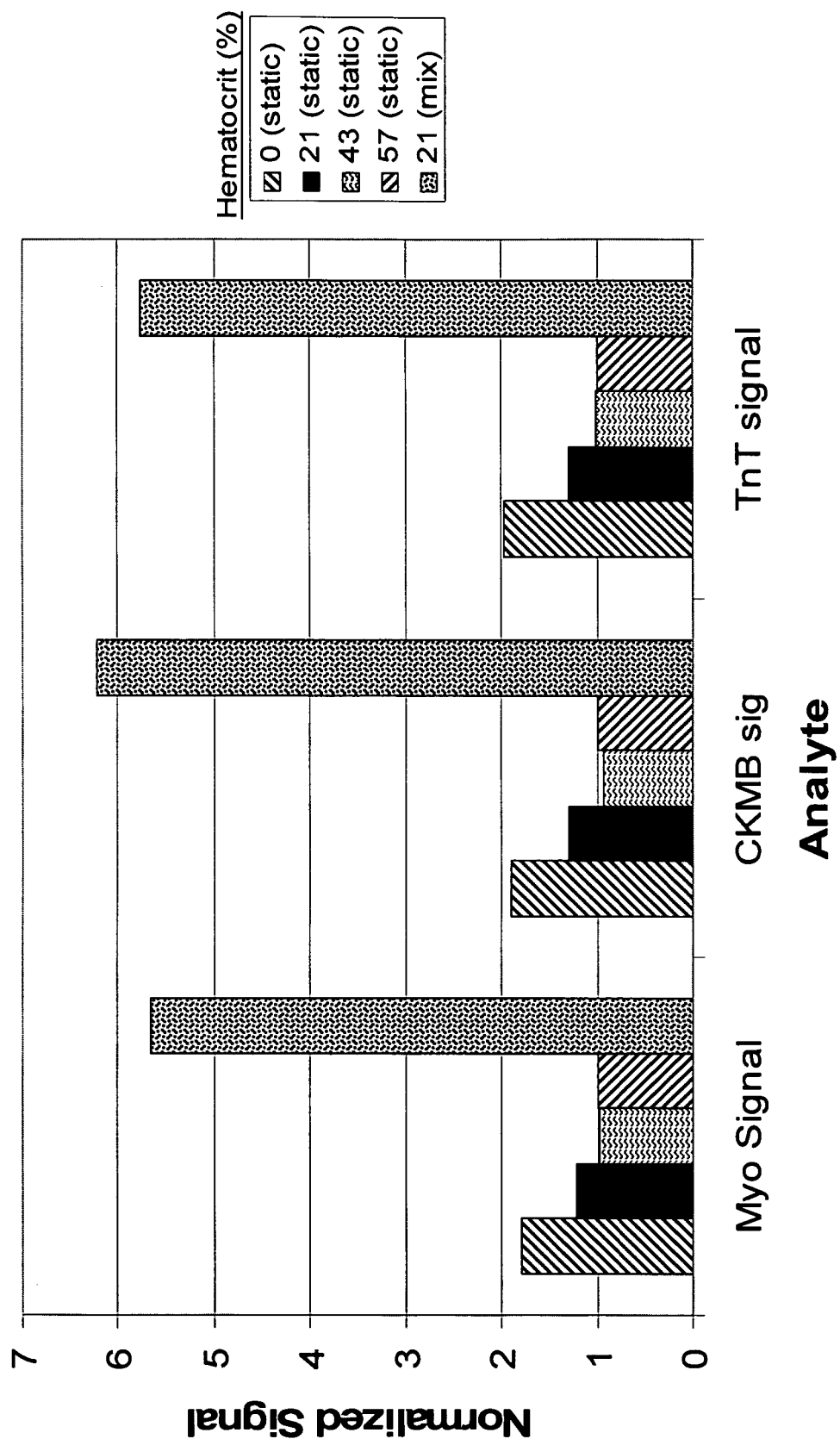
FIG. 6 compares one-step electrochemiluminescence assays for myoglobin, TnT and CKMB in whole blood samples carried out using static incubation conditions or mixing. The plot shows ECL signal (vertical axis) for each analyte (horizontal axis) at four hematocrit levels.

The samples were transferred to cartridges for measurement and analyzed using a one step assay format with a 4 minutes static incubation (without moving the sample fluid over the immobilized capture antibodies). FIG. 6 shows the normalized signals for each sample type along with the signal for a control experiment with mixing. The results show that there is a dependence on hematocrit; the signal for a given plasma level decreases with increasing hematocrit and the corresponding decrease in the amount of analyte per volume of blood. In contrast, assays run while flowing samples over the capture antibodies showed no dependence on hematocrit (see, Example 1).

Comparative Example 4

One-Step Sandwich Immunoassay for Cardiac Markers in Whole Blood Samples; End-Point Assay Whole blood (14250 uL with a hematocrit of 43.4%) was spiked with 600 uL of the pooled cardiac marker solution and 150 uL of the BSA/bovine IgG blocking solution. Four test samples having the same plasma levels of cardiac markers but different hematocrit levels were prepared from the spiked whole blood by a procedure analogous to that described in the Materials and Methods. The following table 4 provides, for each of the samples, the hematocrit, the concentration of each of the analytes in the blood sample (blood concentration) and the concentration of each of the analytes in the plasma fraction (plasma concentration).

TABLE 4

| Sample | Hematocrit (%) | Blood Concentration (ng/mL) | | | Plasma Concentration (ng/mL) | | |
|---|---|---|---|---|---|---|---|
| | | Myo | CKMB | TnT | Myo | CKMB | TnT |
| 1 | 0 | 173 | 15.3 | 2.7 | 173 | 15 | 2.7 |
| 2 | 21 | 137 | 12.0 | 2.1 | 173 | 15 | 2.7 |
| 3 | 41 | 102 | 9.0 | 1.6 | 173 | 15 | 2.7 |
| 4 | 62 | 66 | 5.8 | 1.0 | 173 | 15 | 2.7 |

Figure 7:
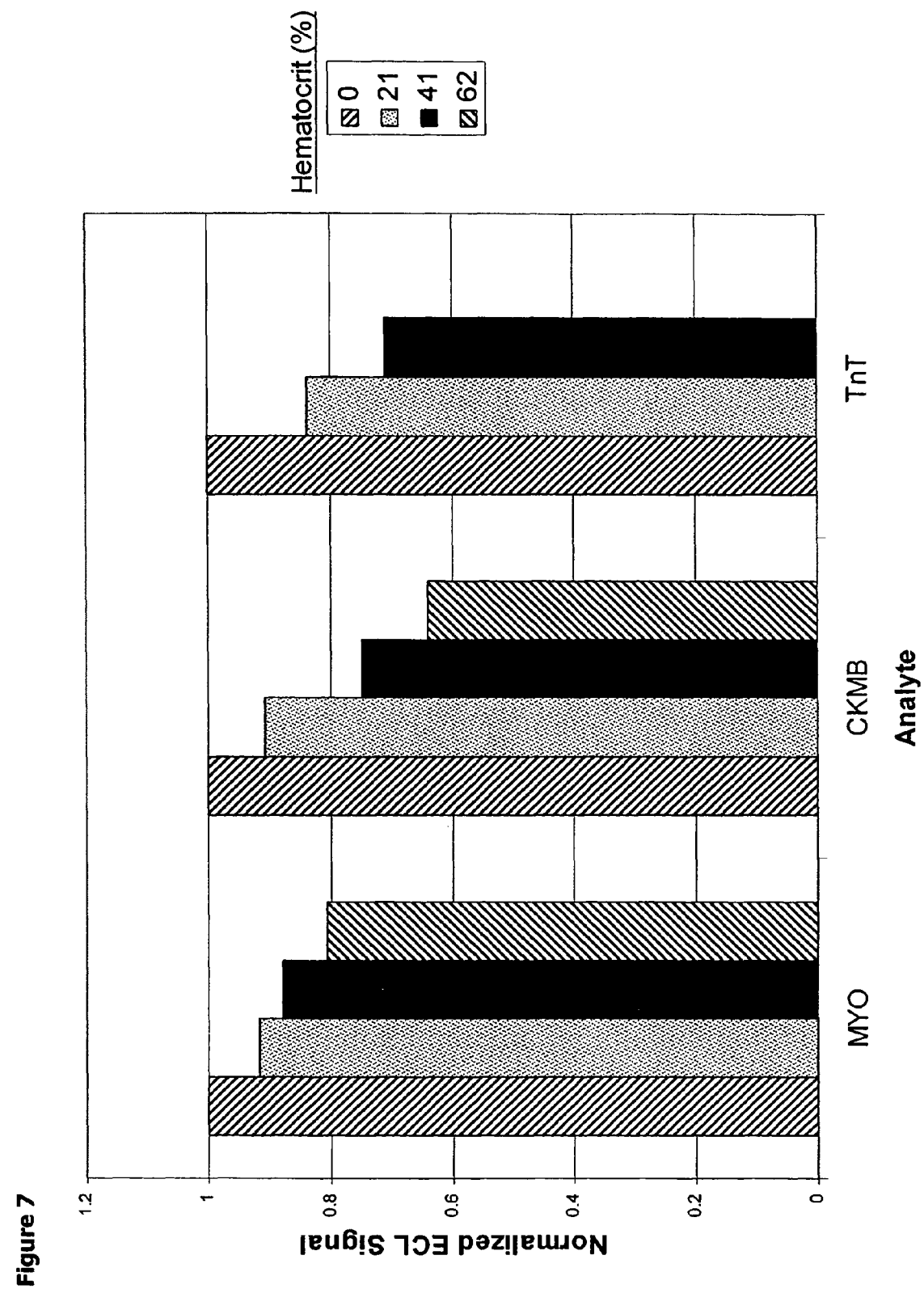
FIG. 7 shows the results of a one-step electrochemiluminescence assay for myoglobin, TnT and CKMB using long incubation times. The plot shows ECL signal (vertical axis) for each analyte (horizontal axis) at four hematocrit levels.

A solution containing the detection antibodies for myoglobin, CKMB and TnT (10 uL) was mixed with 150 uL of each sample to give final concentrations over the total sample volume of 20, 5, and 3 ug/mL for the myoglobin, TnT and CKMB antibodies, respectively. An aliquot (150 uL) of each mixture was transferred to a cartridge for measurement and the assays were conducted using a one step assay format with a one 10 hour incubation time (sufficient time for the binding reactions to proceed to near completion). FIG. 7 shows the normalized signals for each sample type and shows that there is a dependence on hematocrit; the signal for a given plasma level decreases with increasing hematocrit and with the corresponding decrease in the total amount of analyte added to the cartridge. In contrast, no dependence on hematocrit was observed when assays were run under the same conditions except that for using a shorter incubation time that only allowed a small fraction of the analyte to bind to the capture antibodies (see, Example 1).

Example 5

Hematocrit-Independent Two-Step Sandwich Immunoassay for Plasma Levels of Cardiac Markers in Whole Blood Samples Whole blood samples with equal plasma levels of cardiac markers but varying hematocrits were prepared as in Example 4. The detection antibody solution had 5 ug/mL of labeled anti-TnT and 3 ug/mL of anti-CKMB. The detection antibody solution also contained anti-TnI and anti-myoglobin detection antibodies; the number of labels per antibody for these two antibodies was, however, too low to get a good signal in the TnI and CKMB assays and these data are not presented.

Figure 8:
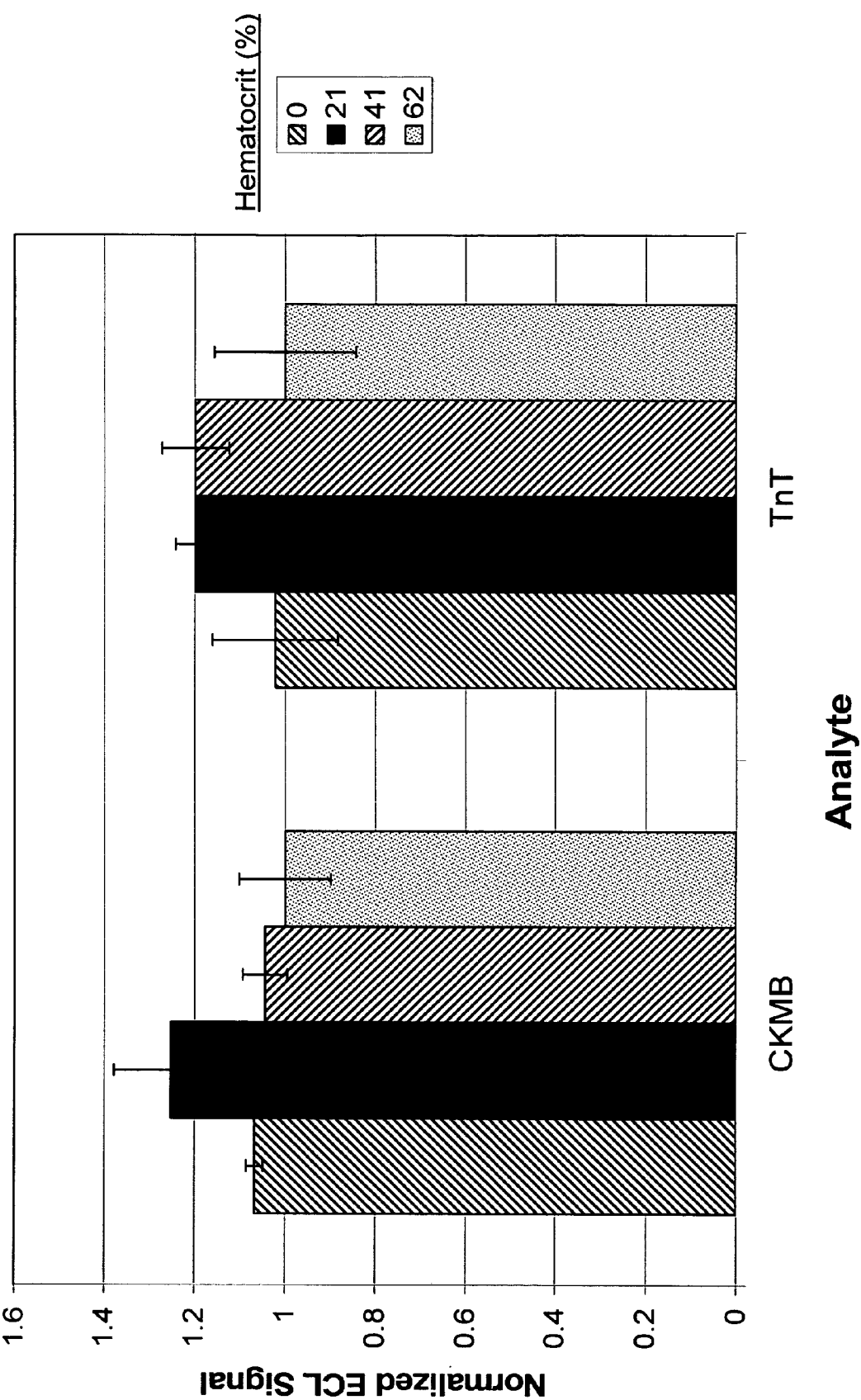
FIG. 8 shows the results of a two-step electrochemiluminescence assay for TnT and CKMB in whole blood samples. The plot shows ECL signal (vertical axis) for each analyte (horizontal axis) at four hematocrit levels.

The assays were conducted in two-step format. FIG. 8 shows the normalized signal. As observed in the analogous one step assay (Example 1), the signals were independent of hematocrit.

Example 6

Hematocrit-Independent Competitive Immunoassay for Plasma Levels of Progesterone in Whole Blood Samples Whole blood (3600 uL with a hematocrit of 45.7%) was spiked with 360 uL of a progesterone solution (80 ng/mL in horse serum) and 40 uL of 50 mg/mL bovine IgG, 5 mg/mL BSA. Four test samples having the same plasma levels of progesterone but different hematocrit levels were prepared from the spiked whole blood by a procedure analogous to that described in the Materials and Methods. The following table 5 provides, for each of the samples, the hematocrit, the concentration of progestoerone in the blood sample (blood concentration) and the concentration of progesterone in the plasma fraction (plasma concentration).

TABLE 5

| Sample | Hematocrit (%) | Blood Concentration (ng/mL) Progesterone | Plasma Concentration (ng/mL) Progesterone |
|---|---|---|---|
| 1 | 0 | 12.2 | 12.2 |
| 2 | 21 | 9.7 | 12.2 |
| 3 | 41 | 7.2 | 12.2 |
| 4 | 54 | 5.6 | 12.2 |

Figure 9:
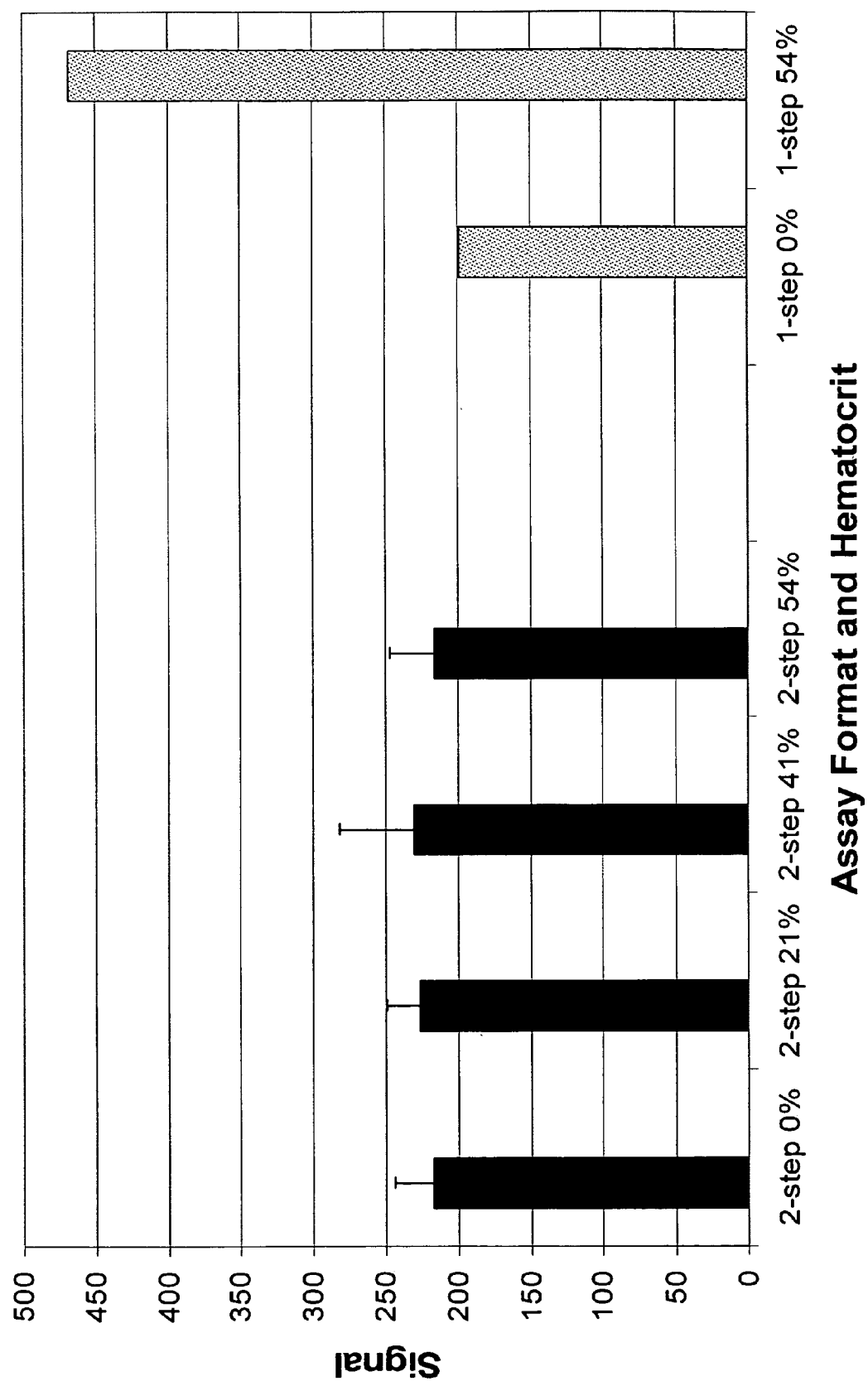
FIG. 9 shows the results of one-step and two-step electrochemiluminescence assays for progesterone. The plot shows ECL signal (vertical axis) for each analyte (horizontal axis) at different hematocrit levels.

One step assays were carried out by adding progesterone labeled with an ECL label (10 ul; 170 ng/ml) to 150 µl of sample and mixing for 3 minutes prior to introduction of the mixture to a cartridge. Two-step assays were carried out by incubating the samples (without labeled progesterone) in the cartridge, washing and then introducing a 10 ng/mL solution of the labeled antigen. FIG. 9 shows that the 2-step competitive assay gives the same signal for samples with the same plasma level of progesterone at different hematocrit levels. In contrast, the results in the one-step assay show a ~2.4-fold greater signal for the high hematocrit (54%) sample relative to the plasma sample. This result is consistent with the higher plasma concentration of labeled antigen (2.3-fold increase) in the high hematocrit sample.

While several embodiments of the invention have been described and illustrated herein, those of ordinary skill in the art will readily envision a variety of other means and structures for performing the functions and/or obtaining the results or advantages described herein, and each of such variations, modifications and improvements is deemed to be within the scope of the present invention. More generally, those skilled in the art would readily appreciate that all parameters, dimensions, materials, configurations, etc. described herein are meant to be exemplary and that actual parameters, dimensions, materials, configurations, etc. will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, provided that such features, systems, materials and/or methods are not mutually inconsistent, is included within the scope of the present invention. Various publications are cited herein, the disclosures of which are incorporated by reference in their entireties. In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

What is claimed is:

1. A method for measuring an analyte of interest in a whole blood sample comprising acts of:
   (a) exposing said whole blood sample to a binding surface within a flow cell by a back and forth flow of said sample over said binding surface so that at least a portion of said sample contacts said binding surface, wherein said binding surface has at least one binding reagent immobilized thereon and said binding reagent binds said analyte of interest;
   (b) immobilizing an amount of said analyte on said surface; and
   (c) measuring said amount of said analyte immobilized to said surface;
   wherein said amount is dependent on the plasma concentration of said analyte in said sample and substantially independent of the hematocrit of said sample.

2. The method of claim 1, wherein the portion of the whole blood sample that contacts the binding surface consists substantially of plasma.

3. The method of claim 1, wherein prior to the exposing act, the whole blood sample has not been subjected to a treatment effecting separation or partitioning of blood cells from the plasma fraction of the whole blood sample.

4. The method of claim 1, wherein said immobilizing act is performed over an interval of time during which less than 30% of said analyte in said sample is immobilized on said surface.

5. The method of claim 1, wherein said immobilizing act is performed over an interval of time which is less than 10 minutes.

6. The method of claim 1, further comprising calibrating said method using calibrator samples with known concentrations of said analyte.

7. The method of claim 6, wherein said calibrator samples are substantially free of red blood cells.

8. The method of claim 1, wherein said measuring is conducted in a sandwich assay format or in a competitive assay format.

9. The method of claim 1, further comprising contacting said sample with a bridging reagent that binds said binding reagent and said analyte.

10. The method of claim 1, further comprising binding said analyte of interest to a labeled binding reagent.

11. The method of claim 10, wherein a label of said labeled binding reagent is selected from a group consisting of: an electrochemiluminescent (ECL) label, luminescent label, fluorescent label, phosphorescent label, radioactive label, light scattering label and combinations thereof.

12. The method of claim 1, further comprising contacting said surface with a labeled analog of said analyte.

13. The method of claim 12, wherein a label of said labeled analog is selected from a group consisting of: ECL label, luminescent label, fluorescent label, phosphorescent label, radioactive label, light scattering label and combinations thereof.

14. The method of claim 1, wherein said binding surface is an electrode surface.

15. The method of claim 1, wherein said surface displays a surface area accessible to said analyte that is at least two-fold larger than the surface area accessible to red blood cells.

16. The method of claim 1, wherein said back and forth flow is laminar.

17. The method of claim 16, wherein said flow has a Reynold's number of less than 100.

18. The method of claim 16, wherein said flow provides a plasma-rich layer adjacent to said surface.

19. The method of claim 1, further comprising displacing said whole blood sample from said surface prior to said measuring said amount of said analyte on said surface.

20. The method of claim 19, wherein said whole blood sample is displaced from said surface by introducing a wash solution.

21. The method of claim 19, wherein after displacing said whole blood sample, the surface is further contacted with a solution containing a labeled binding reagent.

22. The method of claim 19, wherein one or more additional analytes are measured in said sample.

23. The method of claim 1, wherein said whole blood sample is undiluted.

24. The method of claim 1, further comprising adding anticoagulants to said whole blood sample.

25. The method of claim 1, wherein said act of exposing said sample to said binding surface comprises contacting at least a portion of the sample with a plurality of binding reagents on one or more binding surfaces, said binding reagents having different specificity for analytes of interest.

26. The method of claim 1, wherein said binding surface faces downward or sidewise during said immobilization act such that red blood cells in said sample settle away from said binding surface.

27. A method for measuring an analyte of interest in a whole blood sample comprising acts of:
   (a) exposing said whole blood sample to a binding surface within a flow cell by a back and forth flow of said sample over said binding surface so that at least a portion of said sample contacts said binding surface, wherein said binding surface has at least one binding reagent immobilized thereon and said binding reagent binds said analyte of interest;
   (b) immobilizing an amount of said analyte on said surface; and
   (c) generating an assay signal that is indicative of said amount of said analyte immobilized to said surface;
   wherein said assay signal is dependent on the plasma concentration of said analyte and substantially independent of the hematocrit of said sample.

28. The method of claim 27, further comprising displacing said whole blood sample from said surface prior to generating said assay signal.

29. The method of claim 27, wherein the portion of the whole blood sample that contacts the binding surface consists substantially of plasma.

30. The method of claim 27, wherein prior to the exposing act, the whole blood sample has not been subjected to a treatment effecting separation or partitioning of blood cells from the plasma fraction of the whole blood sample.

31. The method of claim 27, wherein said immobilizing act is performed over an interval of time during which less than 30% of said analyte in said sample is immobilized on said surface.

32. The method of claim 27, wherein said immobilizing act is performed over an interval of time which is less than 10 minutes.

33. The method of claim 27, further comprising calibrating said method using calibrator samples with known concentrations of said analyte.

34. The method of claim 33, wherein said calibrator samples are substantially free of red blood cells.

35. The method of claim 27, further comprising contacting said sample with a bridging reagent that binds said binding reagent and said analyte.

36. The method of claim 27, further comprising binding said analyte of interest to a labeled binding reagent.

37. The method of claim 36, wherein a label of said labeled binding reagent is selected from a group consisting of: electrochemiluminescent (ECL) label, luminescent label, fluorescent label, phosphorescent label, radioactive label, light scattering label and combinations thereof.

38. The method of claim 27, further comprising contacting said surface with a labeled analog of said analyte.

39. The method of claim 38, wherein a label of said labeled analog is selected from a group consisting of: ECL label, luminescent label, fluorescent label, phosphorescent label, radioactive label, light scattering label and combinations thereof.

40. The method of claim 27, wherein said binding surface is an electrode surface.

41. The method of claim 27, wherein said surface displays-a surface area accessible to said analyte that is at least two-fold larger than the surface area accessible to red blood cells.

42. The method of claim 27, wherein said back and forth flow is laminar.

43. The method of claim 42, wherein said flow has a Reynold's number of less than 100.

44. The method of claim 42, wherein said flow provides a plasma-rich layer adjacent to said surface.

45. The method of claim 27, further comprising displacing said whole blood sample from said surface prior to said measuring said amount of said analyte on said surface.

46. The method of claim 45, wherein said whole blood sample is displaced from said surface by introducing a wash solution.

47. The method of claim 45, wherein after displacing said whole blood sample, the surface is further contacted with a solution containing a labeled binding reagent.

48. The method of claim 45, wherein one or more additional analytes are measured in said sample.

49. The method of claim 27, wherein said whole blood sample is undiluted.

50. The method of claim 27 further comprising adding anticoagulants to said whole blood sample.

51. The method of claim 27, wherein said act of exposing said sample to said binding surface comprises contacting at least a portion of the sample with a plurality of binding reagents on one or more binding surfaces, said binding reagents having different specificity for analytes of interest.

52. The method of claim 27, wherein said binding surface faces downward or sidewise during said immobilization act such that red blood cells in said sample settle away from said binding surface.

53. A method comprising acts of:
creating a back and forth flow of a whole blood sample comprising or suspected of comprising an analyte of interest over a surface within a flow cell, wherein said blood flow segregates blood cells contained in the sample away from the surface to create a plasma rich first region of the sample and a blood cell rich second region of the sample, wherein said surface comprises at least one binding reagent immobilized thereon and said binding reagent binds said analyte of interest; and
measuring a concentration of said analyte of interest in said plasma rich first region.

54. A method comprising acts of:
exposing a whole blood sample comprising or suspected of comprising an analyte of interest to a surface by flowing said whole blood sample over said surface within a flow cell in a back and forth motion, wherein said surface comprises at least one binding reagent immobilized thereon and said binding reagent binds said analyte of interest;
maintaining blood cells contained in said sample away from at least a portion of said surface to create (i) a first region of said sample in contact with said first surface, and (ii) a second region of said sample separated from said first region, wherein the concentration value of blood cells in said second region substantially exceeds the concentration value of blood cells in said first region; and
measuring a concentration of said analyte of interest in fluid present in said first region of the sample.

* * * * *